United States Patent [19]

Bartroli et al.

[11] Patent Number: 5,070,139
[45] Date of Patent: Dec. 3, 1991

[54] 2,4-DISUBSTITUTED 1,3-DIOXOLANES

[75] Inventors: Javier Bartroli; Manuel Anquita; Elena Carceller, all of Barcelona, Spain

[73] Assignee: J. Uriach & Cia. S.A., Barcelona, Spain

[21] Appl. No.: 515,379

[22] Filed: Apr. 27, 1990

Related U.S. Application Data

[62] Division of Ser. No. 257,092, Oct. 13, 1988, Pat. No. 4,940,706.

[30] Foreign Application Priority Data

Oct. 13, 1987 [ES] Spain .................................. 8702901

[51] Int. Cl.⁵ ........................ C07F 9/06; A61K 31/685
[52] U.S. Cl. ........................................ 549/221; 546/22; 546/23; 548/112; 548/113
[58] Field of Search ...................... 549/221; 546/22, 23; 548/112, 113; 514/336, 365, 467, 79, 80, 89, 93

[56] References Cited

U.S. PATENT DOCUMENTS 3,666,748  5/1972  Honojo et al. ........................ 548/111

FOREIGN PATENT DOCUMENTS 138559  4/1985  European Pat. Off. .
147768  6/1985  European Pat. Off. .
146258  7/1985  European Pat. Off. .
157609  9/1985  European Pat. Off. .

OTHER PUBLICATIONS

Takeda Chemical Industries, Ltd., Chemical Abstract 98:210009j.
Chacko, G., J. Org. Chem., (1967), 32:1623.
Hiltrop, K., Ber. Bunsenges. Phys. Chem., (1978), 82:883.
Marx, M. H., (University of Kansas), Ph.D Thesis, (1985), pp. 29, 30, 86.
Ono Pharmaceutical Co. Ltd., Chem. Abst. 98-54397b, (1983).
Takeda Chemical Industries, Ltd., Chem. Abst. 98-210009b, (1983).
Najima et al., Chem. Abst. 103-142311w, (1985).
Ono Pharmaceutical Co. Ltd., Chem. Abst. 104-51069c, (1986).
Yanopol'skaya et al., Chem. Abst. 87-147531d, (1977).
Grachev et al., Chem. Abst. 88-74379u, (1977).
Nifantév et al., Chem. Abst. 88-151972m, (1978).
Predroditelev et al., Chem. Abst. 93-238767a, (1980).
Nguyen Hoang Phuong et al., Chem. Abst. 84-179591c, (1975).
Grachev et al., Chem. Abst. 86-43672p, (1976).
Nifantév et al., Chem. Abst. 86-155149e, (1977).
Baranova et al., Chem. Abst. 86-184850g, (1977).
Nomura et al., Chem. Abst. 104-88143g, (1986).
Barner et al., Chem. Abst. 104-88939n, (1986).

*Primary Examiner*—Cecilia Shen
*Attorney, Agent, or Firm*—Rothwell, Figg, Ernst & Kurz

[57] ABSTRACT

The present invention describes novel 2,4-disubstituted 1,3-dioxolanes having the formula I

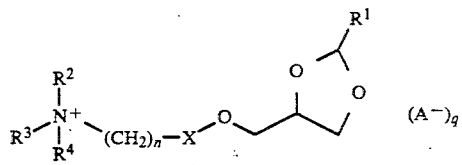

wherein $R^1$ represents a long chain alkyl group; X is a covalent single bond, a carbonyl group, a carboxyl group, a carbamoyl group or a $-O-P(=O)(O^z)-$ group; z is a negative charge ($-$) when q is zero, or z is an hydrogen atom when q is one; n is an integer from 2 to 10; $R^2$, $R^3$ and $R^4$ are lower alkyl groups, or $R^2R^3R^4N^{3\oplus}$ represents an aromatic cyclic ammonium group or $R^2R^3R^4N^+$ represents a non-aromatic cyclic ammonium group in which two of the groups ($R^2$, $R^3$ or $R^4$) form a non-aromatic ring together with the quaternary nitrogen atom; and $A^-$ is a pharmaceutically acceptable anion. These compounds are in vitro inhibitors of the platelet aggregation induced by the platelet activating factor (PAF) and, thus, useful for the treatment of the diseases in which this substance is involved. On the other hand, some of these compounds have hypotensive activity without provoking activation of the platelets.

3 Claims, No Drawings

2,4-DISUBSTITUTED 1,3-DIOXOLANES

This is a division of application Ser. No. 257,092, filed Oct. 13, 1988, now U.S. Pat. No. 4,940,706.

FIELD OF THE INVENTION

The present invention relates to new derivatives of 2,4-disubstituted 1,3-dioxolane with a potent antagonist activity of the platelet activating factor (PAF) and/or a hypotensive activity similar to PAF, together with a process for their preparation. The invention also relates to the pharmaceutical preparations which contain these compounds, and their use in the treatment of diseases in which PAF is involved, such as allergic and bronchial asthma, platelet aggregation disorders, septic shock, hypertension, etc.

BRIEF DESCRIPTION OF THE PRIOR ART

The platelet activating factor (PAF), or (1-O-alkyl-2-acetyl-sn-glyceryl-3-phosphorylcholine), also called acetyl glyceryl ether phosphorylcholine (AGEPC) or PAF-acether is a natural phospholipid synthesized by different cells (basophiles, macrophages, neutrophiles, platelets) and tissues (heart, lung and kidney) of the organism. (Roubin et al. in "Lymphokines" Ed. E. Pick, Acad. Press. New York, p. 249, 1983; Vargaftig et al., *Ann. N.Y. Acad. Sci.*, 1981, 370, 119; Pinckard et al., *Int. Arch. Allergy Appl. Immun.*, 1981, 66, 127.

PAF was described for the first time as a potent platelet aggregating agent (Benveniste et al., *J. Exp. Med.*, 1972, 136) and later it was demonstrated that it had other biological activities in vivo such as peripheral vasodilatation, increase of the vascular permeability, induction of bronchoconstriction and hyperreactivity of the respiratory tract (Mazzoni et al., Proc. Physiol. Soc. Univ. Coll. Meet., March 1985). PAF also products immediate hypotension followed by pulmonary and renal hypertension in rats (Blank et al., *Biochem. Biophys. Res. Commun.*, 1979, 90, 1194), guinea pigs (Feuerstein, et al., *Circul. Shock*, 1984, 13, 255), rabbits (Muirhead et al., *Hypertension*, 1981, 3, 107) and dogs (Otsuka et al., *J. Exp. Med.*, 1972, 136, 1356), and it has been rated as the most potent ulcerogenic agent described until now.

Consequently, PAF is a mediator that is implicated in a large set of pathological processes such as asthma, septic shock, transplant rejection, thrombosis, ulceration, inflammation and renal diseases.

Even though its mechanism of action is still not known with precision, some studies show that the biological activities of PAF involve the existence of a specific receptor. Recently, it has been possible the isolation of one of these receptors from human platelets and it has been identified as a protein with a molecular weight of 160.000 daltons (Nishihira et al., *Tohoku J. Exp. Med.*, 1985, 147, 145). On the other hand, the capacity to inhibit the binding of ³H-PAF to their receptors is well correlated with the amount of PAF needed to provoke the in vitro and in vivo observed effects. These facts indicate that the compound that act as specific antagonists of PAF could result of interest for the treatment of all those pathological processes related directly or indirectly with PAF.

Until now, some families of non cyclic derivatives of glycerol have demonstrated to have PAF antagonist activity (for example, the compounds described in EP 147768, EP 146258, EP 138559, EP 157609, JP 57/165394, JP 58/133116, JP 58/35116, among others).

The new compounds of the present invention not only are structurally different from any of the described compounds in the above mentioned prior art but also, and surprisingly, show a remarkable antagonist activity of PAF and/or an hypotensive action. In fact, never before 2,4-disubstituted derivatives of 1,3-dioxolane have been used as PAF antagonist substances.

On the other hand, there are two references in the literature (*J. Org. Chem.*, 1967, 32, 1623; *Ber. Bunsenges. Phys. Chem.*, 1978, 82, 883) in relation with a similar structure to the ones described in the present invention. Nevertheless, these compounds have never been used as PAF antagonist agents.

DESCRIPTION OF THE INVENTION

The present invention relates to novel 2,4-disubstituted derivatives of 1,3-dioxolane having the general formula I

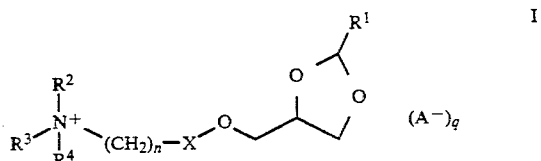

where
- $R^1$ represents a linear or branched alkyl, alkenyl or alkynyl group, of 10 to 24 carbon atoms;
- X is a simple covalent linkage (that is, it does not represent any group) or is one of the following groups $-C(=O)-$, $-O-C(=O)-$, $-NH-C(=O)-$, $-NH^5-C(=O-)$, or $-O-P(=O)(O^z)-$, $R^5$ being a lower alkyl or acyl group and with the condition that when z is a negative charge $(-)$, q is zero, and when Z is an hydrogen atom, q is one;
- n is an integer 2 to 10;
- $R^2$, $R^3$ and $R^4$ are lower alkyl groups (with the exception that, when simultaneously $R^1$ is $n-C_{15}H_{31}$, $n-C_{15}H_{29}$ or $C_{17}H_{33}$ and X is $-O-P(=O)(O^z)-$, then $R^2$, $R^3$ and $R^4$ can not be three methyl groups),
- or $R^2R^3R^4N^+$ represents an aromatic cyclic ammonium group (like thiazolium, benzothiazolium, oxazolium, pyridinium, quinolinium or isoquinolinium), that can contain one or more substituents in the ring (lower alkyl, hydroxyl, lower hydroxyalkyl, amino, lower aminoalkyl, carbamoyl or ureido),
- or $R^2R^3R^4N^+$ represents a non-aromatic cyclic group, in which two of the substituents ($R^2$, $R^3$ or $R^4$) form a ring together with the nitrogen atom (like morpholinium) and the remaining group is hydrogen or a lower alkyl group;
- $A^-$ is a pharmaceutically acceptable anion such as halide (chloride, bromide or iodide), lower alkylsulfonate (like p-toluenesulfonate) or carboxylate.

In this context the terms lower alkyl and lower acyl groups designate, respectively, the R-and RCO—groups in which R is linear or branched and has 1 to 5 carbon atoms.

If desired, the anion $A^-$ can be interchanged with another anion by ion exchange, to afford, in that way, other salts, all of which are considered part of the present invention.

The title compound I have two asymmetrical carbons in the dioxolane ring that can produce four stereoisomers. The present invention includes these stereoisomers as well as their mixtures.

Although the present invention includes all of the above mentioned compounds, the following are specially preferred: Those in which $R^1$ is a linear alkyl chain, in particular those having 14 to 20 carbon atoms; those in which X is a covalent bond or a —C(=O)— group or a —O—C(=O)— group or a —NH—C(=O)— group or a —NR$^5$—C(=O)— group and n goes between 3 and 8; those in which X is a —O—P(=O)(O$^z$)— group and n is 2 to 4; those in which $R^2R^3R^4N+$ is an aromatic cyclic ammonium group, particularly a thiazolium group; those in which A$^-$ is an arylsufonate anion, particularly a p-toluenesulfonate anion, and those in which A$^-$ is an iodide anion. Furthermore, among all of them they are still more preferred the specific compounds whose formulas are represented below, together with the number corresponding to the example in which their preparation is described.

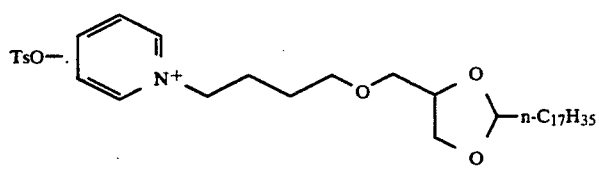

1

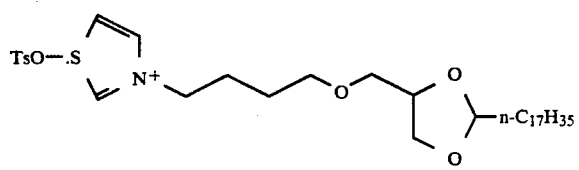

2

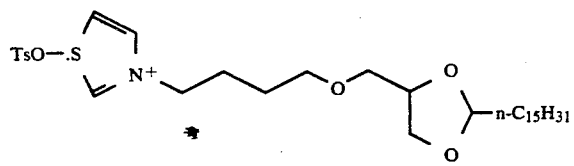

3

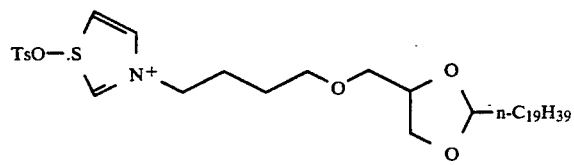

4

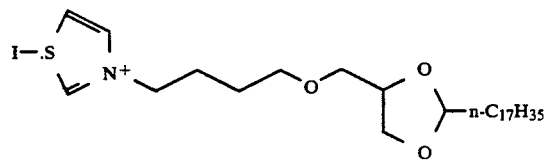

5

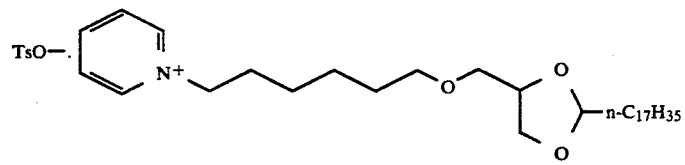

6

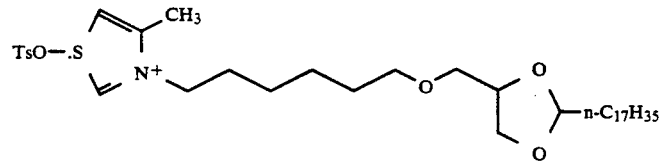

7

-continued
8
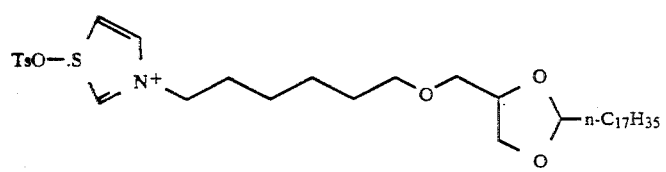
9
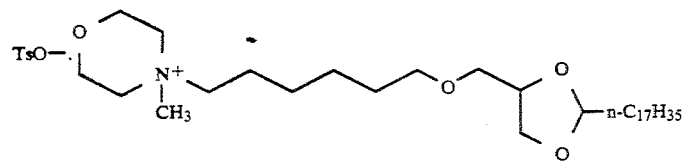
10
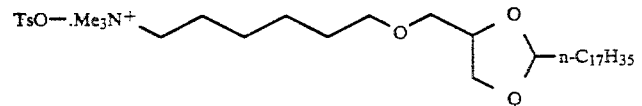
11
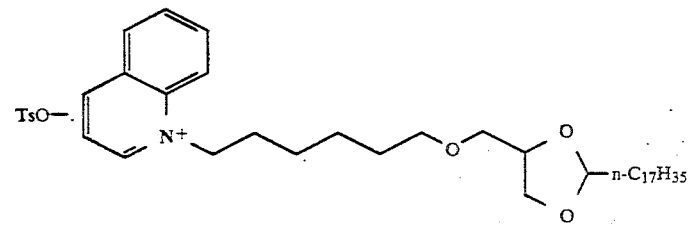
12
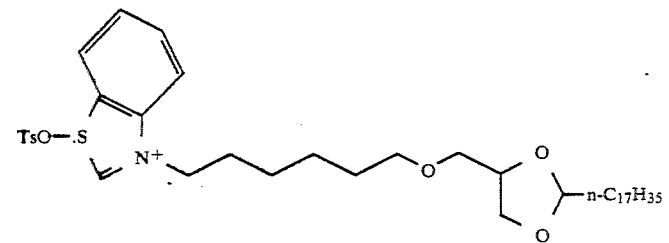
13
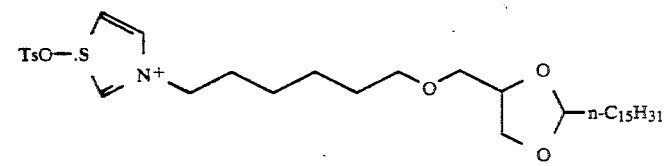
14
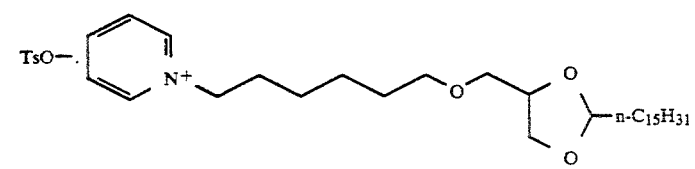
15
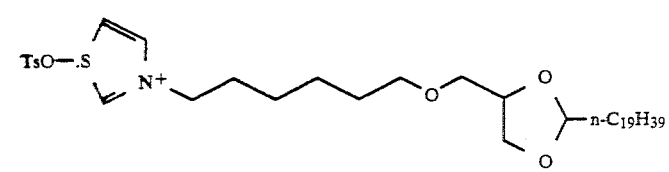

-continued
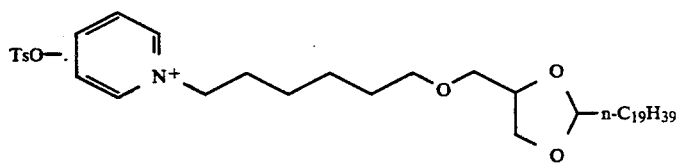
16
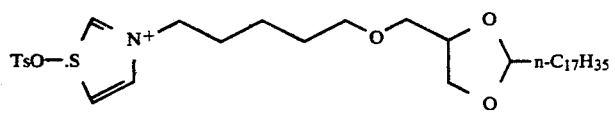
17
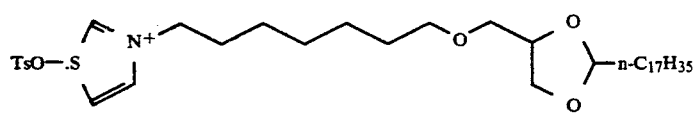
18
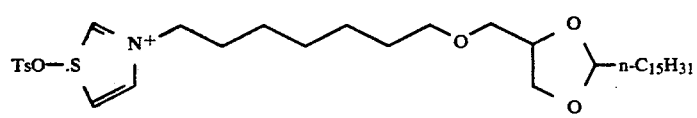
19
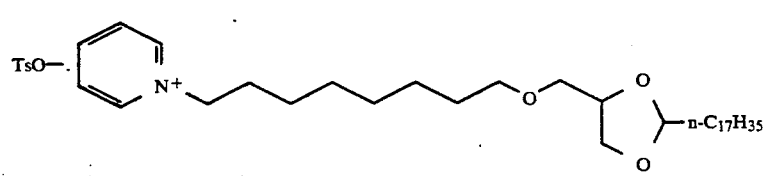
20
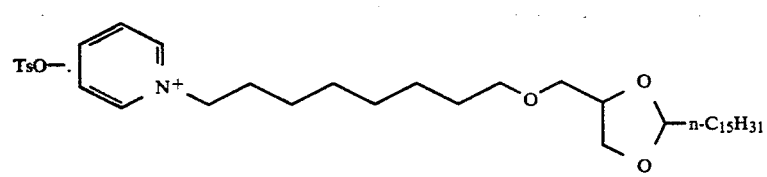
21
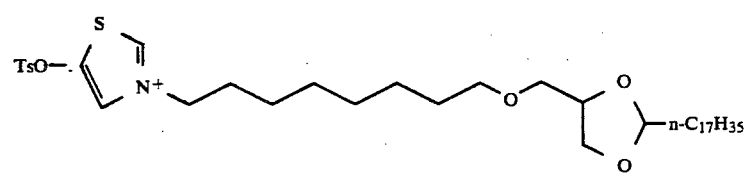
22
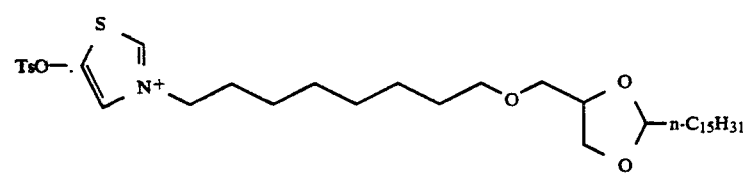
23
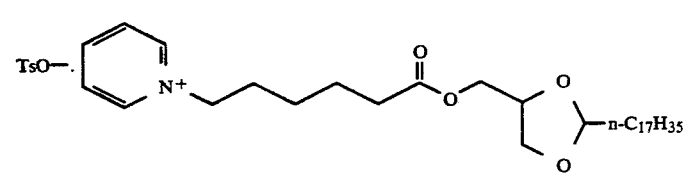
24
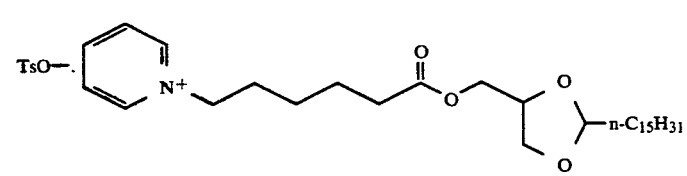
25

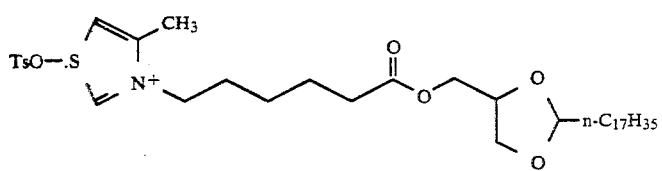
26
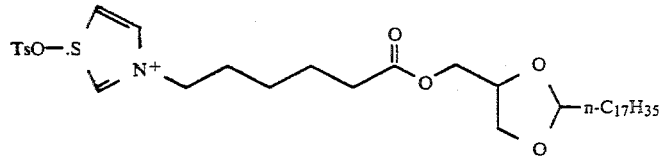
27
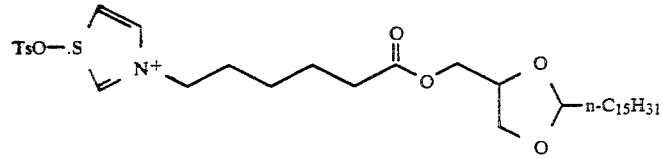
28
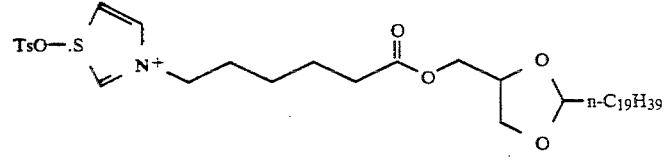
29
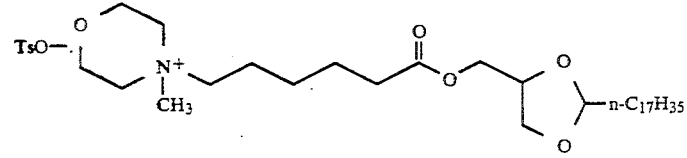
30
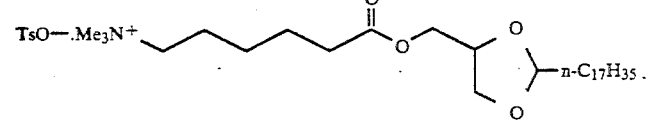
31
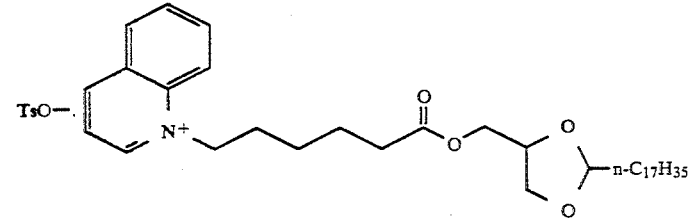
32
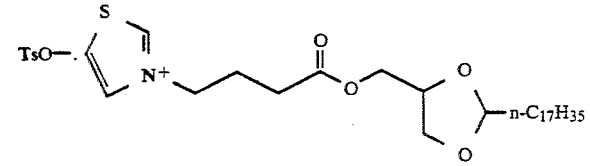
33
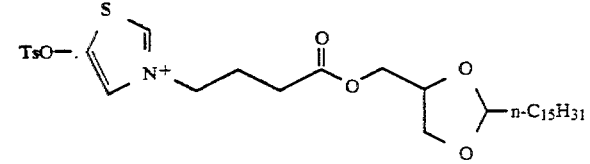
34

-continued
35
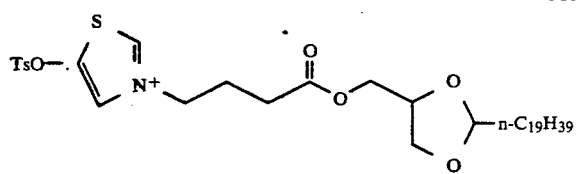
36
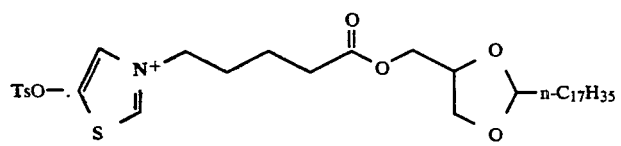
37
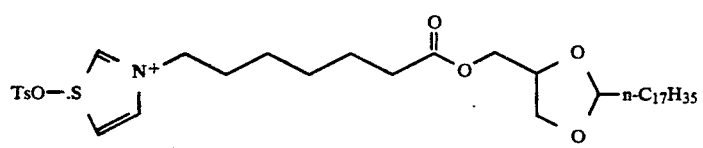
38
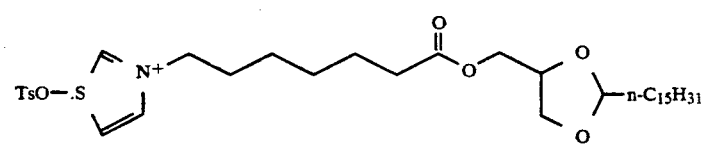
39
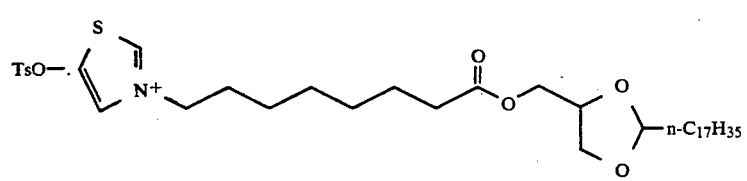
40
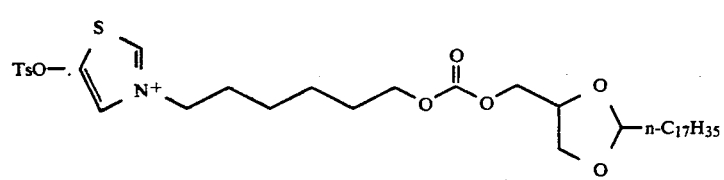
41
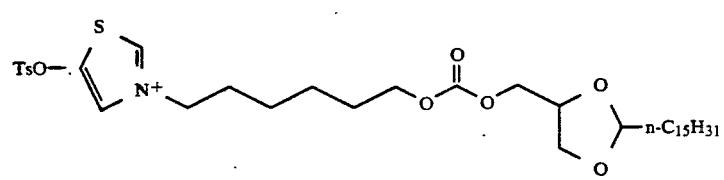
42
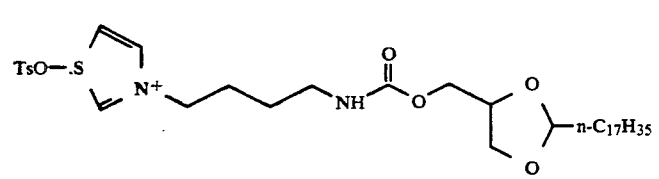
43
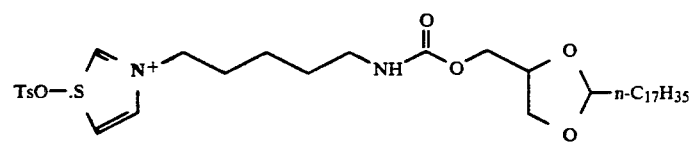
44
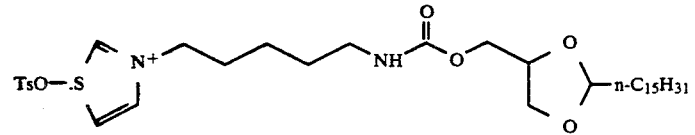

-continued

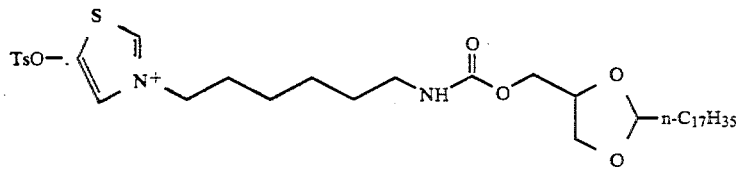

45

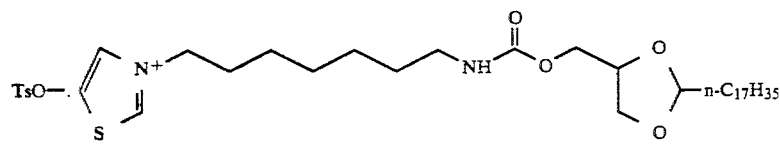

46

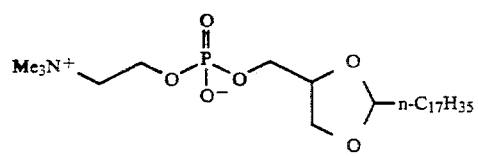

47

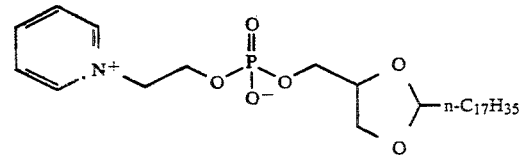

48

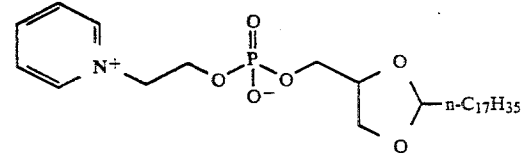

49

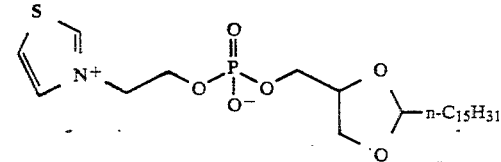

50

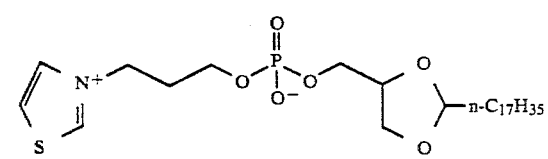

51

We have found that the compounds of the present invention are in vitro inhibitors of the platelet aggregation induced by PAF. On the other hand, these compounds have the capacity to revert the hypotension induced by PAF in anesthetized rats. These facts make them useful as PAF antagonists in the treatment of the diseases in which this substance is involved. Furthermore, some of the mentioned compounds show hypotensive activity as indicated by their capacity to produce a decrease of the blood pressure. Nevertheless and contrary to PAF, the latter compounds do not activate the platelets, supporting their use as antihypertensive agents.

The title compounds I are obtained when an intermediate of general formula

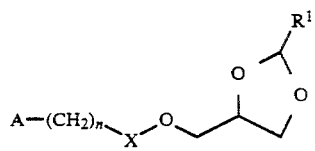

where A is a suitable leaving group, such as halogen (chloro, bromo or iodo), lower alkylsulfonate (like phenylsulfonate or p-toluenesulfonate) or carboxylate and the remaining symbols have the above mentioned meaning, is treated with a nitrogen-containing base $R^2R^3R^4N^+$ where $R^2$, $R^3$ and $R^4$ have the above mentioned meaning, in an appropriate solvent (aprotic dipolar solvents like acetonitrile or dimethylformamide; aromatic hydrocarbons like benzene, toluene or xylene; chlorinated aliphatic hydrocarbons like chloroform or dichloromethane; ethers like tetrahydrofuan), or using said base as the solvent; the reaction is done at a temperature ranging from 40° C. to the boiling temperature of the solvent, during a period of time that can range from 1 to 48 h.

The above mentioned intermediate can be obtained from the corresponding (±)-cis, trans-2-alkyl-1,3-dioxolane-4-methanol (II) by treatment with different known reagents, depending on the nature of the X group, as described in the attached scheme.

Several compounds having the general formula II have been previously described in the literature. For example, II ($R^1$=n—$C_{17}H_{35}$) has been obtained in homoquiral form starting from D-mannitol in several steps (*Chem. Pharm. Bull.*, 1984, 32, 791–4). We have synthesized the corresponding racemic mixture in one single step starting from inexpensive glycerol or solketal by reaction with octadecanal in the presence of a catalytic amount of acid. Octadecanal is not commercially available but in can be easily obtained by oxidation of n-octadecanol with PCC (*Tetrahedron Lett.*, 1975, 31, 2647–50). In a similar way, and using the corresponding linear aldehyde, the different compounds of formula II can be obtained.

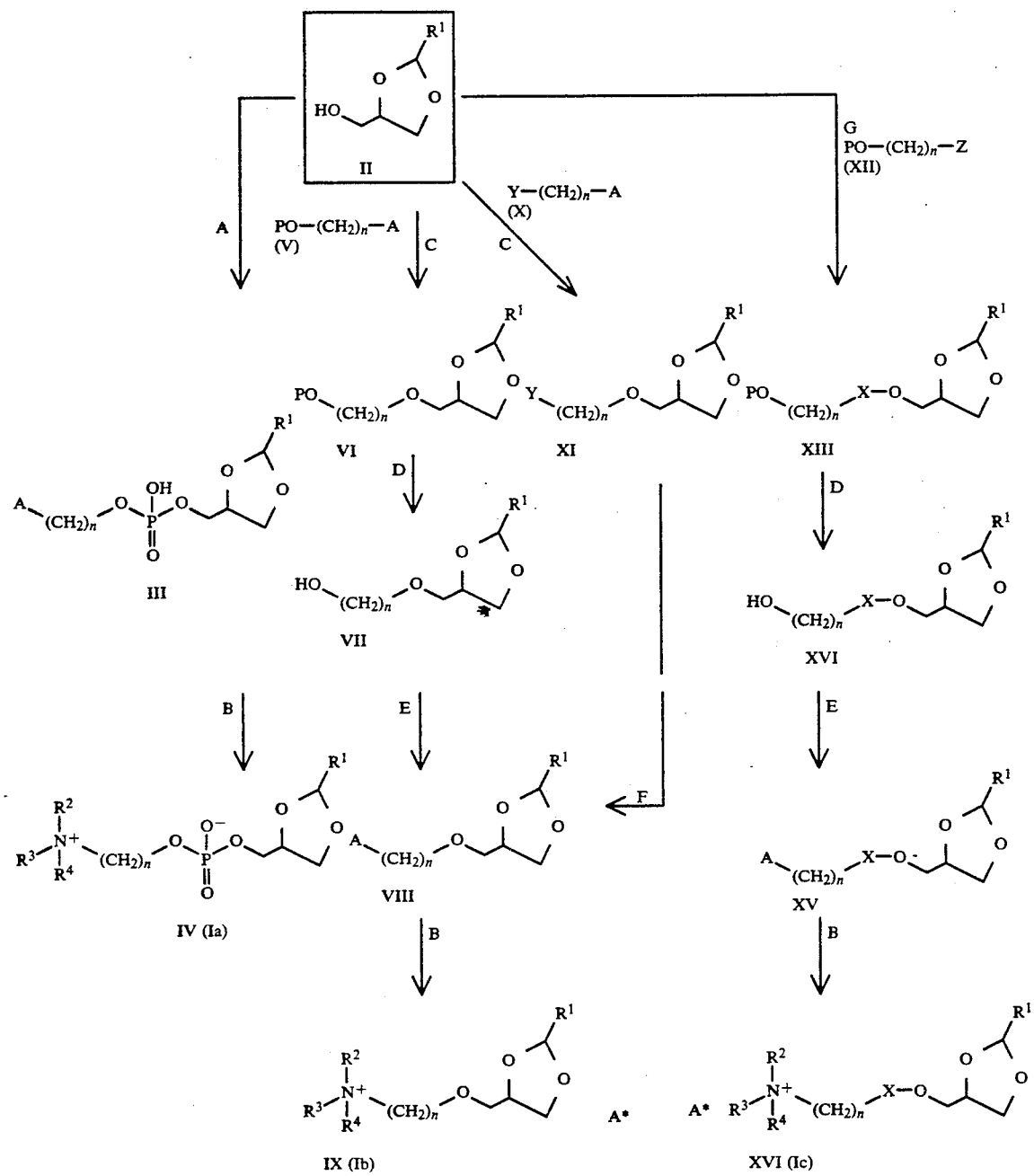

The title compounds I in which X is —O— —P(=O)-($O^z$)— and n is 2 to 4 (subfamily Ia), can be obtained in two steps starting from compound II. This sequence includes a first step (step A) in which compound II is reacted with a w-bromoalkyldichlorophosphate, obtained in a similar way to the preparation of 2-bromoethyldichlorophosphate, described in the literature (*Pharm. Acta Helv.*, 1958, 33, 349-56). The reaction is done in the presence of an amine, such as triethylamine or pyridine, in a inert organic solvent, such as an aromatic hydrocarbon, for example benzene, toluene or xylene, an halogenated aliphatic hydrocarbon, such as carbon tetrachloride, chloroform or dichloromethane, or an ethereal solvent, such as diethylether. The reaction can be carried out at a temperature of from 0° C. to the boiling point of the solvent for a period of time between 5 min and 5 h. Compound III is then obtained by hydrolysis using a base like sodium acetate in water, or a mixture of a miscible solvent like tetrahydrofuran and water, at 0°-100° C. for 1 min to 6 h. In the second step (step B) the compound obtained in step A is treated with a nitrogen-containing base followed by silver carbonate to give the quaternary ammonium salt IV. The reaction can be conveniently done using the suitable base as solvent or in the pressure of a cosolvent such as benzene, acetonitrile or dimethylformamide at a temperature ranging from 50° C. to the boiling point of the solvent.

The title compounds I where X is a single covalent bond and q is 1 (subfamily Ib), can be obtained starting from compound II in four steps, as shown in the scheme. Thus, in a first step (step C) compound II is treated with compound V, where P is an adequate hydroxyl protecting group and A is a leaving group. Compounds V are not commercially available but they can be easily obtained in two steps starting from the corresponding 1,n-alkanediol. For example, when P is benzyl and A is p-toluenesulfonyloxy, the corresponding compound V can be obtained starting with the corresponding 1,n-alkanediol by monobenzylation (1 equiv. NaH, 1 equiv. BnBr, cyclohexane) and tosylation (TsCl, pyr, $CH_2Cl_2$). Step C, then, involves reaction of compound II with a strong base, such as sodium hydride and, next, with the mentioned compound V in a non-protic polar solvent, such as dimethylformamide. The reaction can be carried out at 50°-120° C. for 1-24 h. In step D, the compound obtained in step C (VI) is dissolved in a protogenic solvent, such as methanol or ethanol, a chlorinated aliphatic hydrocarbon, such as dichloromethane, or an ethereal solvent, such as tetrahydrofuran, and it is hydrogenated at 1 atmosphere or under pressure in the presence of a metal catalyst, such as palladium, on a support substance, such as finely divided carbon. The reaction can be conveniently carried out at room temperature for a period of time ranging between 15 min. and 22 h. In step E, the hydroxyl group of compound VII, obtained in step D, is transformed into a leaving group A. When A is p-toluenesulfonyloxy, compound VIII can be easily obtained by reaction of compound VII with p-toluenesulfonyl chloride in the presence of a proton scavenger, such as pyridine or triethylamine. The reaction is done in pyridien or in an inert organic solvent such as a chlorinated aliphatic hydrocarbon, for example, dichloromethane, or an ethereal solvent, such as diethyl ether. In relation to the experimental conditions, the reaction is done at a temperature ranging between 0° and 30° C. for a period of time between 6 and 24 h. Finally, the preparation of compounds of the subclass Ib includes the reaction of compound VIII obtained in step E with the desired amine, following the process described for step B (see above).

Alternatively, the compounds of subclass Ia can be synthesized starting from compound II and a compound having the general formula X, where A and Y are two leaving groups and A is better leaving group than Y. This last compound could be non commercially available, but it can be easily prepared starting from the suitable alcohol. When Y is Cl and A is p-toluenesulfonyloxy, the compound is prepared according to a published procedure (*Zh. Obshch. Khim.*, 1968, 38, 1517-1520). The reaction of compound II with compound X is done in the same way as described in step C. The next step, step F, involves the transformation of the poor leaving group Y into a better leaving group A to give compound VIII. When Y is Cl and A is I, this transformation is done by treatment of compound XI with an excess of sodium iodide in a solvent such as acetone, in which the resulting sodium chloride is not soluble. The reaction is done at 25°-56° C. for 6-24 h.

The title compounds I where X is —C(=O)—O—C(=O)—, —NH—C(=O)— or —NR$^5$—C(=O)—, and q is 1 (subfamily Ic), can be obtained starting from compound II in four steps, as shown in the scheme. In the first step (step G) compound II is treated with a compound having the general formula XII, where P is a hydroxyl protecting group and Z is a —C(=O)Cl, —N=C=O or —O—C(=O)Cl group. Compounds XII are not commercially available but they can be easily obtained from the corresponding 1,n-alkenediol. Thus, when P is benzyl and Z is any of the three functions above mentioned, the corresponding compound XII can be obtained starting from the corresponding 1,n-alkanediol by monobenzylation (1 equiv. NaH, 1equiv. BnBr, cyclohexane) and transformation into any of the three functionalities following well established classical methods (Org. Synth. III, 547 for the preparation of—C(=O)Cl, Org. Synth. III, 847 for —N=C=O and Org. Synth. III, 167 for —O—C(=O)Cl). Therefore, step G involves the reaction of compound II with compound XII in the presence of a proton scavenger, such as triethylamine or pyridine, in an inert organic solvent such as an aromatic hydrocarbon, for example benzene, toluene or xylene, a chlorinated aliphatic hydrocarbon, for example chloroform or dichloromethane, or an ethereal solvent, for example, tetrahydrofuran or diethyl ether. The reaction can be done at a temperature ranging between 0° C. and the boiling point of the solvent for 1-24 h. Following essentially the same synthetic route used for the preparation of compounds of subfamily Ib (that is to sayd steps D,E, and B) one may obtain the compounds of subfamily Ic, of general formula XVI.

It should be emphasized that, according to the above mentioned process, the preparation of the title compounds I is very straightforward and involves the use of unexpensive starting materials such as glycerol. This represents a clear advantage in relation to other PAF antagonist whose preparation require expensive starting materials and/or the use of a sophisticated methodology.

The title compounds I are useful as PAF inhibitors, as demonstrated by their ability to inhibit the in vitro platelet aggregation induced by PAF in rabbit platelets according to test 1:

Test 1: Inhibition of Platelet Aggregation Induced by PAF.

The blood is obtained by cardiac puncture of male New Zealand albino rabbits (between 2 and 2.5 Kg of weight) and coagulation is prevented by adding 1 part of 3.16% sodium citrate dihydrate in 9 parts of blood. The platelet rich plasma (PRP) is prepared by blood centrifugation at 250 xg for 10 min. at 4° C. and it is diluted with platelet poor plasma (PPP) obtained by additional centrifugation at 300xg for 10 min. The amount of platelets is adjusted to $3 \times 10^{-5}/mm^3$. The platelet aggregation induced by PAF ($C_{18}$, prepared in our laboratory) (16 nM, final) is determined by the Born nephelometric technique (*J. Physiol.*, 1962, 162, 67) using a aggregometer Chronolog 500. The activities of the inhibitors are expressed as $IC_{50}$, that is to say the concentration of the drug needed to inhibit the platelet aggregation in a 50%. The results are shown in table 1:

TABLE 1

| Compound number | $IC_{50}$ ($\mu M$) |
|---|---|
| 1 | 5.5 |
| 2 | 6.0 |
| 5 | 5.0 |
| 6 | 3.3 |
| 7 | 3.1 |
| 8 | 1.4 |
| 9 | 18 |
| 10 | 5.5 |
| 11 | 3.9 |
| 12 | 16 |
| 20 | 14 |
| 22 | 5.1 |
| 24 | 2.6 |
| 26 | 2.5 |
| 27 | 1.3 |
| 30 | 21 |
| 31 | 7.8 |
| 32 | 2.5 |
| 47 | 180 |
| 48 | 180 |

Furthermore, it has been found that the title compounds I are inhibitors of the hypotension induced by PAF according to test 2.

Test 2—Inhibition of the Hypotensive Effect Induced by PAF in normotense Rats.

Male Sprague Dawley rats, of 180-220 g of weight, anesthetized with sodium pentobarbital (50 mg/Kg, i.p. 1 mL/100 g) have been used. In order to measure the average arterial pressure, a polyethylene catheter is introduced into the carotide artery. The arterial pressure is recorded with the help of a transducer connected with a R611 Beckman polygraph. The tested compounds are administrated through the femoral vein 3 min. Before the injection of PAF (0.5 mg/Kg, i.v.). The inhibition of the hypotension induced by PAF of the different compounds with a 5 mg/Kg dose, i.v., is shown in table 2.

TABLE 2

| Compound number | Dose (mg/Kg, i.v.) | % Inhibition |
|---|---|---|
| 1 | 5 | 24 |
| 6 | 5 | 42 |
|  | 5 | 88 |
| 8 | 2.5 | 75 |
|  | 1.25 | 46 |
|  | 5 | 72 |
| 24 | 2.5 | 58 |
|  | 5 | 100 |
| 27 | 1.25 | 75 |
|  | 0.63 | 28 |
| 32 | 5 | 80 |

On the other hand, the title compounds I are capable to revert the hypotension induced by PAF as shown in test 3.

Test 3—Reversion of the Hypotensive Effect Induced by PAF in Normotense Rats

The experimental design is similar to that of test 2, except in that the compound to be tested is given by intravenous injection 1 min. After the injection of PAF. In the controls the blood pressure recovers 80% of the basal level 6.2 min. after the injection of PAF. The effect of the tested compounds is expressed as the dose required to reduce in a 50% the time of recovery of the basal blood pressure ($ID_{50}$).

TABLE 3

| Compound number | $ID_{50}$ (mg/Kg, i.v.) |
|---|---|
| 8 | 0.30 |
| 27 | 0.16 |

Solid compositions according to the present invention for oral administration include compressed tablets, dispersible powders, granules and capsules. In tablets, one or more of the active component (s) is admixed with at least one inert diluent such as lactose, starch, mannitol, microcrystalline cellulose or calcium phosphate; granulating and disintegrating agents for example corn starch, alginic acid; binding agents for example, starch, gelatine, microcrystalline cellulose or polyvinylpyrrolidone; and lubricating agents for example magnesium stearate, stearic acid or talc. The tablets may be coated by known techniques to delay disintegration and absorption in the gastrointestinal tract and, thereby, provide a sustained action over a longer period. Gastric film-coated or enteric film-coated can be made with sugar, gelatin, hydroxypyropylcellulose, or acrilic resins. Tablets with a sustained action may also be obtained using an excipient which provides regressive osmosis, such as the galacturonic acid polymers. Formulations for oral use may also be presented as hard capsules of absorbable material, such as gelatin, wherein the active ingredient is mixed with an inert solid diluent and lubricating agents, or pasty materials, such as etoxylated saturated glycerides, and they may also present controlled release. Soft gelatin capsules are possible wherein the active ingredient is mixed with water or an oil medium, for example peanut oil, liquid paraffin or olive oil.

Dispersible powders and granules suitable for preparation of a suspension by the addition of water provide the active ingredient in admixtured with a dispersing or wetting agent; suspending agent, such as sodium carboxymethylcellulose, methylcellulose, hydroxypropylmethylcellulose, sodium alginate, polyvinylpirrolidone, gum tragacanth, xantham gum, gum acacia; and one or more preservatives, such as methyl or n-propyl-p-hydroxybenzoate. Additional excipients, for example sweetening, flavoring and coloring agents may also be present.

Liquid compositions for oral administration include emulsions, solutions, suspensions, syrups and elixirs containing inert diluents commonly used, such as distilled water, ethanol, sorbitol, glycerol, propylene glycol. Such compositions may also comprise adjuvants such as wetting agents, suspending agents, sweetening, flavouring, perfuming, preserving agents and buffers.

Other compositions for oral administration include spray compositions which may be prepared by known methods and which comprise one or more active compound (s). The spray compositions will contain a suitable propellant.

Preparations for injection according to the present invention for parenteral administration include sterile aqueous or non-aqueous solutions, suspensions or emulsions, in a non-toxic parentally-acceptable diluent or solvent. Examples of aqueous solvents or suspending media are distilled water for injection, the Ringer's solution and isotonic sodium chloride solution. Examples of non-aqueous solvents or suspending media are propylene glycol, polyethylene glycol, vegetable oils such as olive oil, or alcohols such as ethanol. These compositions may also include adjuvants such as wetting, preserving, emulsifying and dispersing agents. They may be sterilized by one of the known methods or manufactured in the form of sterile solid compositions which can be dissolved in sterile water or some other sterile injectable medium immediately before use. When all of the components are sterile, the injectables will maintain the sterility if they are manufactured in sterile environment.

A compound of the invention may be also administered in the for of suppositories for rectal administration of the drug; creams, ointments, jellies, solutions or suspensions for topical use and pessaries for vaginal administration.

Following are some representative preparations for tablets, capsules, syrups, aerosols and injectables. They can be prepared following standard procedures and they are useful as inhibitors of platelet activating factor.

Tablets

| Title compound I | 100 mg |
|---|---|
| Dibasic calcium phosphate | 125 mg |
| Sodium starch glycolate | 10 mg |
| Talc | 12.5 mg |
| Magnesium stearate | 2.5 mg |
| | 250.0 mg |

Hard Gelatin Capsules

| Title compound I | 100 mg |
|---|---|
| Lactose | 197 mg |
| Magnesium stearate | 3 mg |
| | 300 mg |

Syrup

| Title compound I | | 0.4 g |
|---|---|---|
| Sucrose | | 45 g |
| Flavouring agent | | 0.2 g |
| Sweetening agent | | 0.1 g |
| Water | to | 100 mL |

Aerosol

| Title compound I | | 4 g |
|---|---|---|
| Flavouring agent | | 0.2 g |
| Propylene glycol | to | 100 mL |
| Suitable propellent | to | 1 unit |

Injectable Preparation

| Title compound I | 100 mg |
|---|---|
| Benzylic alcohol | 0.05 mL |
| Propylene glycol | 1 mL |
| Water to | 5 mL |

The following examples illustrate, but do not limit, the preparation of the compounds of the present invention.

EXAMPLE 1

(±)-cis, trans-1[4-[(2-heptadecyl-1,3-dioxolane-4-yl)methoxy]-butyl]piridinium 4-methylbenzenesulphonate a) (±)-cis, trans-2-heptadecyl-1,3-dioxolane-4-methanol To a solution of anhydrous glycerol (10.13 g, 0.11 mmol) and octadecanal (20.1 g, 0.075 mol) in dry benzene (100 mL) was added camphorsulfonic acid (1.74 g, 10% equiv. mol). The mixture is stirred at room temperature for 18 h and then 1M pH 7 phosphate buffer (20 mL) was added. The aqueous phase was separated and the organic layer was washed with a saturated solution of sodium chloride and dried over anhydrous sodium sulfate. The solvent was evaporated to afford 23.6 g (92%) of a solid that contained a small amount of unreacted octadecanal. Purification by flash-chromatography yielded 11.6 g (45%) of pure product.

mp: 53.6°–54.5° C.; IR (KBr) v : 3240, 2916, 2846, 1464, 1129, 1043, 958, 721 cm$^{-1}$; $^1$H-NMR (60 MHz, CDCl$_3$) δ (TMS) 5.2–4.9 (m, 2H, OCHO), 4.4–4.0 (m, 1H, CH$_2$CHO), 4.0–3.6 (m, 4H, HOCH$_2$CHCH$_2$), 2.2–2.0 (s, 1H, OH), 1.9–0.8 (m, approx. 35H).

Analysis calculated for C$_{21}$H$_{42}$O$_3$: C 73.62%; H 12.36%. Found: C 73.83%; H 12.58%.

b) (±)-cis, trans-2-heptadecyl-4-[(4-benzyloxy)butoxy)methyl]-1,3-dioxolane

To a suspension of sodium hydride (55% oil dispersion, 1.70 g, 39 mmol) in dimethylformamide (30-mL) in an argon atmosphere it was added the compound obtained in 1a (10.27 g, 30 mmol) followed by a solution of 4-(benzyloxy)butyl 4-methylbenzenesulfonate (13.7 g, 41 mmol) in dry dimethylformamide (40 mL). The mixture was heated at 80° C. producing the appearance of hydrogen gas. After 15 min. of stirring at this temperature, the reaction mixture was left at room temperature for 18 h. Water was added (100 mL) and the mixture was extracted with ether (2×100 mL). The combined ethereal layers were washed with 1M sodium bicarbonate (100 mL), then with a saturated solution of sodium chloride and dried with anhydrous sodium sulfate. After solvent evaporation, 16.31 g of a yellow oil were obtained. Purification by flash-chromatography (silica gel, ethyl acetate:hexane 12:1) afforded 11.2 g (74%) of a pure waxy product.

mp: approx. 30° C.; IR (KBr) v: 2913, 2848, 1467, 1450, 1365, 1122, 730, 696 cm$^{-1}$; $^1$H-NMR (60 mHz, CDCl$_3$) δ (TMS): 7.4 (s, 5H, Ar), 5.1–4.8 (m, 1H, OCHO), 4.52 (s, 2H, ArCH$_2$), 4.3–4.0 (m, 1H), 4.0–3.6 (m, 1H), 3.6–3.3 (m, 6H), 2.0–0.8 (m, approx. 39H).

Analysis calculated for C$_{32}$H$_{56}$O$_4$: C 76.14%; H 11.18%. Found: C 75.74%; H 11.55%.

c) (±)-cis, trans-4-[(2-heptadecyl-1,3-dioxolane-4-yl)methoxy-1-butanol

A solution of the compound obtained in example 1b (8.60 g, 17.0 mmol) and 5% palladium over carbon (700 mg) in dichloromethane (200 mL) was hydrogenated at 100 psi for 3 h. The suspension was filtered and the solvent was concentrated to give a white solid (6.50 g, 92%).

mp: 34°–44° C.; IR (KBv) v: 3405, 2914, 2846, 1466, 1128, 1067, 957, 894, 832, 720 cm$^{-1}$; $^1$H-NMR (60 mHz, CDCl$_3$)ω (TMS) 5.1–4.8 (m, 1H, OCHO), 4.4–3.4 (m, 9H), 1.9–0.8 (m, approx. 39H).

Analysis calculated for C$_{25}$H$_{50}$O$_4$ : C 72.40%; H 12.15%. Found: C 72.10%; H 12.47%.

d) (±)-cis, trans-4-[(2-heptadecyl-1,3-dioxolane-4-yl)methoxy]butyl 4-methylbenzenesulfate To a cooled solution (0° C.) of the crude obtained in example 1c (0.72 g) in dry pyridine (2 mL) and dichloromethane (10 mL) a solution of 4-methylbenzenesulfonyl chloride (0.343 g, 1.802 mmol) in dichloromethane (3mL) was added. The mixture was stirred during 18 h at room temperature, and then water (50 mL) was added. After ether extraction (2×50 mL), the ethereal layer was washed with 1N HCl (25 mL), a saturated solution of sodium chloride (50 mL) and dried over anhydrous sodium sulfate. Solvent concentration and flash-chromatography purification (silica gel, ethyl acetate:hexane, 1:2) afforded 0.45 g (55%, 2 steps)

mp: 51.4°–53.7° C.; IR (KBv) v: 2914, 2846, 1595, 1467, 1356, 1184, 1170, 1122, 1106, 958, 842, 668 cm$^{-1}$; $^1$H-NMR (60 MHz, CDCl$_3$)δ (TMS) 7.8 (d, J=8 Hz, 2H, Tos), 7.4 (d, J=8 Hz, 2H, Tos), 5.1–4.8 (m, 1H, OCHO), 4.7–3.4 (m, 9H), 2.5 (s, 3H, Tos-CH$_3$), 2.0–0.7 (m, approx. 39H).

Analysis calculated for C$_{32}$H$_{56}$O$_6$S: C 67.57%; H 9.92%. Found: C 66.23%; H 10.08%.

e) Preparation of the title compound

A solution of the compound obtained in example 1d (0.18 g, 0.316 mmol) in dry pyridine (1 mL) was refluxed for 3 h under argon atmosphere. The solvent was evaporated and the resulting solid was dissolved in the minimum amount of dichloromethane and was precipitated with ether. The resulting solid was filtered and vacuum-dried yielding the title compound (86% yield).

mp: 98°–105° C; IR (KBr) v 3443 (H$_2$O), 3073, 2914, 2846, 1637, 1485, 1464, 1211, 1199, 1124, 1034, 1011, 683, cm$^{-1}$; $^1$H-NMR (60 MHz, CDCl$_3$)δ (TMS) 9.4–9.1 (m, 2H, pyr), 8.7–7.8 (m, 3H, pyr), 7.8 (d, J=8 Hz, 2H, Tos), 7.2 (d, J=8 Hz, 2H, Tos), 5.0–4.5 (m, 3H, NCH$_2$, OCHO), 4.3–3.3 (m, 7H, CH$_2$OCH$_2$CHCH$_2$), 2.3 (s, 3H, Tos-CH$_3$), 2.2–0.8 (m, approx. 39H).

Analysis calculated for C$_{35}$H$_{59}$NO$_6$S$_2$.2H$_2$O: C 62.20%; H 9.39%; N 2.07%. Found: C 62.06%; H 9.36%; N 2.24%.

EXAMPLE 2

(±)-cis, trans-3-[4-[(2-heptadecyl-1,3-dioxolane-4-yl)methoxy]butyl]thiazolium 4-methylbenzenesulfonate Following he procedure described in example 1e but using thiazole instead of pyridine the title compound of this example was obtained as a cream-colored solid (84% yield).

mp: 79°–86° C.; IR (KBv) v: 3443 (H$_2$O), 3097, 3052, 2914, 2846, 1465, 1226, 1192, 1120, 1034, 1010 cm$^{-1}$; $^1$H-NMR (60 MHz, CDCl$_3$)δ (TMS) 10.6 (br s, 1H, SCH═N), 8.6–8.2 (m, 2H, SCH═CNH), 7.8 (d, J=8 Hz, 2H, Tos), 7.2 (d, J=8 Hz, 2H, Tos), 5.0–4.4 (m, 3H, NCH$_2$, OCHO), 4.4–4.0 (m, 1H, OCHCH$_2$O), 4.0–3.2 (m, 6H), 2.3 (s, 3H, Tos-CH$_3$), 2.2–0.8 (m, approx. 39H).

Analysis calculated for C$_{35}$H$_{59}$NO$_6$S$_2$.2H$_2$O: C 62.06%, H 9.39%, N 2.07%. Found: C 62.06%; H 9.36%; N 2.24%.

EXAMPLE 3

(±)-cis, trans-3-[4-[(2-pentadecyl-1,3-dioxolane-4-yl)methoxy]butyl]thiazolium 4-methylbenzenesulfonate Following the methodology described in example 2, but using hexadecanal instead of octadecanal, the title compound of this example was obtained with a similar yield.

EXAMPLE 4

(±)-cis, trans-3-[4-(2-nonadecyl-1,3-dioxolane-4-yl)methoxy]butyl]thiazolium 4-methylbenzenesulfonate Following the methodology described in example 2, but using eicosanal instead of octadecanal, the title compound of this example was obtained with a similar yield.

EXAMPLE 5

(±)-cis, trans-3-[4-[(2-heptadecyl-1,3-dioxolane-4-yl)methoxy]butyl)thiazolium iodide.

a) Preparation of (±)-4-[(4-chlorobutoxy)methyl]-2,2-dimethyl-1,3-dioxolane.

To a cooled suspension (0° C.) of sodium hydride (55% oil dispersion, 510 mg, 11.7 mmol) in dry tetrahydrofuran (15 mL) under an argon atmosphere it was added (±)-2,2-dimethyl-1,3-dioxolane-4-methanol (1.18 g, 9 mmol) dissolved in dry tetrahydrofuran (15 mL). The mixture was stirred at room temperature for 30 min. and refluxed during 1 min. After cooling the mixture at room temperature 4-chlorobutyl 4-methylbenzenesulfonate (3.12 g, 12 mmol) in dry tetrahydrofuran (15 mL) was added and the mixture was refluxed for 18 h. 1M pH 7 phosphate buffer was added and the organic solvent was evaporated. The group was treated with water and hexane and the organic phase was separated, dried over anhydrous sodium sulfate and concentrated to afford 1.73 g of a thick oil being a 3:1 mixture of desired product and 4-chlorobutyl 4-methylbenzenesulfonate (determined by NMR spectroscopy).

b) (±)-cis, trans-4-[(4-chlorobutoxy)methyl]-2-heptadecyl-1,3-dioxolane.

To a solution of the product obtained in example 5a (1.73 g, aprox. 5.8 mmol) and octadecanal (1.55 g, 5.8 mmol) in dry toluene (16 mL) was added camphorsulfonic acid (126 mg, 0.54 mmol). The mixture was stirred at room temperature for 18 h and, after, 1M pH 7 phosphate buffer was added. The organic phase was separated and dried over anhydrous sodium sulfate. By evaporation of the solvent a semi-solid group was obtained that was purified by flash-chromatography (silica gel, ethyl acetate:hexane, 1:20) affording 2.02 g (51%, 2 steps) of the desired product in a white semisolid form.

IR(KBr) v 2916, 2847, 1465, 1119, 721 cm$^{-1}$; $^1$H-NMR (60 MHz, CDCl$_3$) δ (TMS) 5.1–4.8 (m, 1H, OCHO), 4.4–4.0 (m), 4.0–3.5 (m), 2.0–0.7 (m, approx. 39H).

c) (±)-cis, trans-2-heptadecyl-4-[(4-iodobutoxy)-methyl]-1,3-dioxolane.

The compound obtained in example 5b (300 mg, 0.69 mmol) was dissolved in acetone (5 mL) and treated with an excess of sodium iodide (518 mg, 3.45 mmol). The mixture was refluxed for 18 h and, then, water (20 mL) and ether (20 mL) were added. The ethereal layer was evaporated and washed with a saturated solution of sodium chloride (20 mL), diluted with hexane, dried over anhydrous sodium sulfate and concentrated giving a waxy solid (300 mg, 83%). IR (KBr) v 2921, 2849, 1462, 1375, 1223, 1119, 721, cm$^{-1}$; $^1$H-NMR (60 mHz, CDCl$_3$) δ (TMS) 5.1–4.7 (m, 1H, OCHO), 4.4–4.0 (m), 4.0–3.4 (m), 3.2 (t, J=7 Hz, ICH$_2$), 2.2–0.7 (m, approx. 39H).

d) Preparation Of The Title Compound

A solution containing the product obtained in example 5c (200 mg, 0.38 mmol) and thiazole (0.2 mL, 2.8 mmol) in dry acetonitrile (2 mL) was stirred at 80° C. for 24 h. The mixture was concentrated in vacuo and the group was diluted with ethanol and precipitated with ether. The resulting solid was filtered and dried yielding 105 mg (45%) of a yellow wax.

IR (KBr) v 3455 (H$_2$O), 3054, 2913, 2846, 1624, 1547, 1465, 1417, 1258, 1124 cm$^{-1}$; $^1$H-NMR (60 MHz, DMSO-d$_6$, CD$_3$OD) δ (TMS) 8.8–8.5 (m, 1H, thiazole), 8.5–8.3 (m, 1H, thiazole), 5.0–4.7 (m, 1H, OCHO), 4.6 (t, J=7 Hz, 2H, NCH$_2$), 4.4–3.9 (m), 3.8–3.2 (m), 2.3–1.8 (m, aprox. 2H), 1.8–0.7 (m, approx. 37H).

EXAMPLE 6

(±)-cis, trans-1-[6-[(2-heptadecyl-1,3-dioxolane-4-yl)methoxy]hexyl]pyridinium 4-methylbenzenesulfonate.

a) (±)-cis, trans-4-[((6-benzyloxyhexyl)oxy)methyl]-2-heptadecyl-1,3-dioxolane.

Following the procedure described in example 1b, but using 6-benzyloxyhexyl 4-methylbenzenesulfonate instead of 4-benzyloxybutyl 4-methylbenzenesulfonate, the desired product was obtained in 40% yield after purification by flash-chromatography (silica gel, ethyl acetate: hexane, 1:7).

IR (KBr) v 3025, 2921, 2850, 1492, 1451, 1359, 1119, cm$^{-1}$; $^1$H-NMR (60 MHz, CDCl$_3$) δ (TMS) 7.35 (s, 5H, Ar), 5.1–4.8 (m, 1H, OCHO), 4.4–4.0 (m), 4.0–3.7 (m), 3.7–3.3 (m), 1.8–0.8 (m, approx. 43H).

Analysis calculated for C$_{34}$H$_{60}$O$_4$: C 76.63%; H 11.35. Found : C 76.33%; H 11.01%.

b) (±)-cis, trans-6-[(2-heptadecyl-1,3-dioxolane-4-il)methoxy]-1-hexanol.

Following the procedure described in example 1c, but using the compound obtained in example 6a instead of the compound obtained in example 1b, a white solid was obtained in 88% yield.

mp : 44.9°–47.5° C.; IR (KBr) v 3338, 2913, 2846, 1468, 1412, 1161, 1130, 1061, 1043, 950, 895, 718 cm$^{-1}$; $^1$H-NMR (60 MHz, CDCl$_3$) δ (TMS) 5.1–4.8 (m, 1H, OCHO), 4.4–3.4 (m, 9H), 1.8–0.8 (m, approx. 43H).

Analysis calculated for C$_{27}$H$_{54}$O$_4$: C 73.24%; H 12.29%. Found C 73.56%; H 12.61%.

c) (±)-cis, trans-6-[(2-heptadecyl-1,3-dioxolane-4-yl)methoxy]-hexyl 4-methylbenzenesulfonate Following the procedure described in example 1d, but using the compound obtained in example 6b instead of compound in example 1c, the corresponding 4-methylsulfonate was obtained in 57% yield as a white solid after flash-chromatography purification (silica gel, ethyl acetate: hexane, 1:2).

mp: 46.9°–49.8° C.; IR(KBr) v 2913, 2847, 1595, 1467, 1410, 1360, 1295, 1186, 1171, 1123, 1107, 956, 839, 820 cm$^{-1}$; $^1$H-NMR (60 MHz, CDCl$_3$) δ (TMS) 7.75 (d, J=8 Hz, 2H, Tos), 7.4 (d, J=8 Hz, 2H, Tos), 5.1–4.9 (m, 1H, OCHO), 4.4–3.7 (m), 3.7–3.3 (m), 2.5 (s, 3H, CH$_3$) 2.0–0.8 (m, approx. 43H).

Analysis calculated for C$_{34}$H$_{60}$O$_6$S: C 68.42%; H 10.13%. Found: C 68.13%; H 10.61%.

d) Preparation of the Title Compound

Following the procedure described in example 1e, but using the compound obtained in example 6c instead of the compound obtained in example 1d, the title compound of this example was obtained as a white solid in 90% yield.

mp: 94°–103° C.; IR (KBr) v 3450 (H$_2$O), 3072, 2914, 2847, 1636, 1485, 1464, 1212, 1200, 1121, 1034, 1011, 819, 683 cm$^{-1}$; $^1$H-NMR (60 MHz, CDCl$_3$) δ (TMS) 9.3–9.1 (m, 2H, pyr), 8.7–7.5 (m, 5H, pyr, Tos), 7.1 (d, J=7 Hz, 2H, Tos), 5.0–4.4 (m, 3H, OCHO, NCH$_2$), 4.4–3.0 (m, 7H, CH$_2$OCH$_2$CHCH$_2$), 2.3 (s, 3H, CH$_3$), 2.0–0.7 (m, approx. 43H).

Analysis calculated for C$_{39}$H$_{63}$NO$_6 \cdot \frac{1}{2}$H$_2$O: C 68.58%; H 9.44%; N 2.05%. Found: C68.58%; H 9.80; N 2.01%.

EXAMPLE 7

(±)-cis, trans-3-[6-[(2-heptadecyl-1,3-dioxolane-4-yl)methoxy]hexyl]-4-methylthiazolium 4-methylbenzenesulfonate Following the procedure described in example 1e, but using the compound obtained in example 6c and 4-methylthiazole, instead of the compound obtained in example 1d and pyridine, respectively, the title compound of this example was obtained as a solid of cream color in 64% yield.

mp: 83°–86° C.; IR (KBr) v 3463 (H$_2$O), 3118, 2915, 2847, 1643, 1573, 1465, 1220, 1173, 1122, 1034, 1010, 818, 685 cm$^{-1}$; $^1$H-NMR (60 MHz, CDCl$_3$) δ (TMS) 10.5 (br s, 1H, SCH=N), 8.0–7.8 (br s, 1H, SCH=C), 7.7 (d, J=8 Hz, 2H, Tos), 7.1 (d, J=8 Hz, 2H, Tos), 5.0–4.7 (m, 1H, OCHO), 4.7–3.2 (m, 9H, NCH$_2$, CH$_2$OCH$_2$CHCH$_2$O), 2.5 (s, 3H, thiazole-CH$_3$), 2.3 (s, 3H, Tos-CH$_3$), 2.0–0.7 (m, approx. 43H).

Analysis calculated for C$_{38}$H$_{63}$O$_2$S$_2$N.2H$_2$O: C 62.52%; H 9.25%; N 1.91. Found: C 62.72%; H 9.25%; N 1.91%.

EXAMPLE 8

(±)-cis, trans-3-[6-[(2-heptadecyl-1,3-dioxolane-4-yl)methoxy]hexyl]thiazolium 4-methylbenzenesulfonate Following the procedure described in example 1e, but using the compound obtained in example 6c and thiazole, instead of the compound obtained in example 1d and pyridine, respectively, the title compound of this example was obtained as a cream-colored solid in 82% yield.

mp: 84°–89° C.; IR (KBr) v 3447(H$_2$O), 3141, 2914, 2846, 1465, 1211, 1196, 1121, 1035, 1011, 818, 684 cm$^{-1}$; $^1$H-NMR (200 MHz, CDCl$_3$) δ (TMS) 10.68 (br s, 1H, N=CHS), 8.28 (br d, 2H, SCH=CHN), 7.75 (d, J=8.1 Hz, 2H, Tos), 7.16 (d, J=8.1 Hz, 2H, Tos), 4.95 (t, J=4.8 Hz, OCHO, minor isomer), 4.86 (t, J=4.7 Hz, OCHO, major isomer), 4.62 (br t, J=7 Hz, 2H, NCH$_2$), 4.2–4.05 (m, 1H, OCH$_2$CHO), 3.88 (dd, J=7.1 Hz, J=7.9 Hz, 1H, major isomer), 3.70 (dd, J=5.4 Hz, J=7.9 Hz, 1H, major isomer), 3.6–3.3 (m), 2.34 (s, 3H, Tos-CH$_3$), 1.95–1.81 (m, 2H), 1.7–1.0 (m, approx. 39H), 0.87 (br t, 3H, CH$_3$).

Analysis calculated for C$_{37}$H$_{61}$NO$_6$S$_2$.H$_2$O : C 63.67%; H 9.09%; N 2.00%. Found: C 63.79%; H 9.48%; N 2.05%.

EXAMPLE 9

(±)-cis, trans-4-[6-[(2-heptadecyl-1,3-dioxolane-4-yl)methoxy]-hexyl]-4-methylmorpholinium 4-methylbenzenesulfonate Following the procedure described in example 1e, but using the compound obtained in example 6c and N-morpholine, instead of the compound obtained in example 1d and pyridine, respectively, the title compound of this example was obtained as a pale orange solid in 82% yield.

mp: 86°–102° C.; IR (KBr) v 3472 (H$_2$O), 2914, 2848, 1464, 1202, 1119, 1065, 1034, 817, 682, 563 cm$^{-1}$; $^1$H-NMR (60 MHz, CDCl$_3$) δ (TMS) 7.8 (d, J=8 Hz, 2H, Tos), 7.2 (d, J=8 Hz, 2H, Tos), 5.1–4.8 (m, 1H, OCHO), 4.5–2.8 (m, 17H), 3.3 (s, 3H, NCH$_3$), 2.35 (s, 3H, CH$_3$-Tos), 1.9–0.7 (m, approx. 43H).

Analysis calculated for C$_{39}$H$_{71}$NO$_7$S.H$_2$O: C 65.43%; H 10.27%; N 1.95%. Found C 65.66%; H 10.62%; N 2.04%.

EXAMPLE 10

(±)-cis, trans-6-[(2-heptadecyl-1,3-dioxolane-4-yl)methoxy]-N,N,N-trimethyl-1-hexanaminium 4-methylbenzenesulfonate Following the procedure described in example 1e, but using the compound obtained in example 6c and a (1:2) mixture of trimethylamine: acetonitrile, instead of the compound obtained in example 1d and pyridine, respectively, the title compound of this example was obtained as a white solid in 74% yield.

mp: 117°–137° C.; IR (KBr) v 3420 (H$_2$O), 2915, 2847, 1482, 1410, 1194, 1120, 1034, 1010, 818, 683, 563 cm$^{-1}$; $^1$H-NMR (60 MHz, CDCl$_3$) δ (TMS) 7.7 (d, J=8 Hz, 2H, Tos), 7.15 (d, J=8 Hz, 2H, Tos), 5.1–4.8 (m, 1H, OCHO), 4.5–3.0 (m, 9H, NCH$_2$, CH$_2$OCH$_2$CHCH$_2$O), 3.2 (s, 9H, (CH$_3$)$_3$N), 2.30 (s, 3H, Tos-CH$_3$), 2.0–0.7 (m, approx. 43H).

Analysis calculated for C$_{37}$H$_{69}$NO$_6$S.½H$_2$O: C 66.83%; H 10.61%; N 2.10%. Found: C 66.59%; H 10.93%; N 2.13%.

EXAMPLE 11

(±)-cis, trans-1-[6-(2-heptadecyl-1,3-dioxolane-4-yl)methoxy]-hexyl]quinolinium 4-methylbenzenesulfonate Following the procedure described in example 1e, but using the compound obtained in example 6c and quinoline, instead of the compound obtained in example 1d and pyridine, respectively, the title compound of this example was obtained as a reddish hygroscopic solid in 92% yield.

mp: 57°–64° C.; IR (KBr) v 3463 (H$_2$O), 3075, 3050, 2915, 2846, 1622, 1592, 1523, 1463, 1405, 1376, 1196, 1120, 1033, 1010, 815, 681 cm$^{-1}$; $^1$H-NMR (60 MHz, CDCl$_3$) δ (TMS) 10.1–9.9 (m, 1H, quinoline), 9.3–9.0 (m, 1H, quinoline), 8.5–7.8 (m, 5H, quinoline), 7.85 (d, J=8 Hz, 2H, Tos), 7.15 (d, J=8 Hz, 2H, Tos), 5.5–4.8 (m, 3H, NCH$_2$, OCHO), 4.3–4.0 (m), 4.0–3.7 (m), 3.7–2.8 (m), 2.3 (s, 3H, Tos-CH$_3$), 2.0–0.8 (m, approx. 43H).

Analysis calculated for C$_{43}$H$_{67}$NO$_6$S.3/4H$_2$O: C 69.83%; H 9.33%; N 1.89%. Found: C 69.91%; H 9.78%; N 1.95%.

EXAMPLE 12

(±)-cis, trans-3-[6-[(2-heptadecyl-1,3-dioxolane-4-yl)methoxy]-hexyl]benzothiazolium 4-methylbenzenesulfonate Following the procedure described in example 1e, but using the compound obtained in example 6c and benzothiazole, instead of the compound obtained in example 1d and pyridine, respectively, the title compound of this example was obtained as a hygroscopic yellowish solid in 65% yield.

mp 60°–67° C.; IR (KBr) v 3419 (H$_2$O), 2915, 2846, 1578, 1508, 1465, 1430, 1193, 1121, 1032, 1010, 815 16, 763, 681 cm$^{-1}$; $^1$H-NMR (60MHz, CDCl$_3$) δ (TMS) 11.3 (br s, 1H, SCH=N), 8.4–7.4 (m, 4H, Ar); 7.72 (d, J=8 Hz, 2H, Tos), 7.05 (d, J=8 Hz, 2H, Tos); 5.1–4.7 (m, 3H, OCHO, NCH$_2$), 4.4–3.2 (m, 7H, CH$_2$OCH$_2$CHCH$_2$O), 2.25 (s, 3H, Tos-CH$_3$), 1.8–0.7 (m, approx. 43H).

Analysis calculated for C$_{41}$H$_{65}$NO$_6$S$_2$.3/2H$_2$O : C 64.87%; H 9.02%; N 1.84%. Found: C 64.91%; H8.61; N 1.98%.

EXAMPLE 13

(±)-cis, trans-3-[6-[(2-pentadecyl-1,3-dioxolane-4-yl)methoxy]-hexyl]thiazolium 4-methylbenzenesulfonate Following the procedure described in example 8, but using hexadecanal instead of octadecanal, the title compound of this example was obtained in a similar yield.

EXAMPLE 14

(±)-cis, trans-1-[6-[(2-pentadecyl-1,3-dioxolane-4-yl)methoxy]-hexyl]pyridinium 4-methylbenzenesulfonate Following the procedure described in example 6, but using hexadecanal instead of octadecanal, the title compound of this example was obtained in a similar yield.

EXAMPLE 15

(±)-cis, trans-3-[6-[(2-nonadecyl-1,3-dioxolane-4-yl)methoxy]-hexyl]thiazolium 4-methylbenzenesulfonate Following the procedure described in example 8, but using eicosanal instead of octadecanal, the title compound of this example was obtained in a similar yield.

EXAMPLE 16

(±)-cis, trans-1-[6-[(2-nonadecyl-1,3-dioxolane-4-yl)methoxy]-hexyl]pyridinium 4-methylbenzenesulfonate Following the procedure described in example 6, but using eicosanal instead of octadecanal, the title compound of this example was obtained in a similar yield.

EXAMPLE 17

(±)-cis, trans-3-[5-[(2-heptadecyl-1,3-dioxolane-4-yl)methoxy]-pentyl]thiazolium 4-methylbenzenesulfonate Following the procedure described in example 1, but using 5-(benzyloxy)pentyl instead of 4-(benzyloxy)butyl 4-methylbenzenesulfonate, the title compound of this example was obtained in a similar yield.

EXAMPLE 18

(±)-cis, trans-3-[7-[(2-heptadecyl-1,3-dioxolane-4-yl)methoxy]-heptyl]thiazolium 4-methylbenzenesulfonate Following the procedure described in example 1, but using 7-(benzyloxy)heptyl instead of 4-(benzyloxy)butyl 4-methylbenzenesulfonate, the title compound of this example was obtained in a similar yield.

EXAMPLE 19

(±)-cis, trans-3-[7-[(2-pentadecyl-1,3-dioxolane-4-yl)methoxy]-heptyl]thiazolium 4-methylbenzenesulfonate Following the procedure described in example 18, but using hexadecanal instead of octadecanal, the title compound of this example was obtained in a similar yield.

EXAMPLE 20

(±)-cis, trans-1-[8-[(2-heptadecyl-1,3-dioxolane-4-yl)methoxy)octyl]pyridinium 4-methylbenzenesulfonate a) (±)-cis, trans,-4-[((8-benzyloxy)octyl)oxy)methyl]-b 2heptadecyl-1,3-dioxolane Following the procedure described in example 1b, but using 8-(benzyloxy)octyl instead of 4-(benzyloxy)-butyl 4-methylbenzenesulfonate, a 30% yield of the product was obtained after flash-chromatography purification (silica gel, ethyl acetate:hexane, 1:10).

mp: 28.8°–29.0° C.; IR (KBr) ν 2921, 2850, 1462, 1406, 1360, 1118, 733, 697; $^1$H-NMR (60 MHz, CDCl$_3$) δ (TMS) 7.4 (s, 5H, Ar), 5.1–4.7 (m, 1H, OCHO), 4.55 (s, 2H, ArCH$_2$), 4.3–4.0 (m, 1H), 4.0–3.7 (m, 1H), 3.7–3.3 (m, 6H), 2.0–0.8 (m, approx. 47H).

Analysis calculated for C$_{36}$H$_{64}$O$_4$: C 77.09%, H 11.50%. Found: C 76.77%; H 11.73%.

b) (±)-cis, trans-8-[(2-heptadecyl-1,3-dioxolane-4-yl)methoxy]-1-octanol

Following the procedure described in example 1c, but using the compound obtained in example 20 instead of the compound obtained in example 1b, a white solid was obtained in 79% yield.

mp: 50.2° C.; IR (KBr) ν 3319, 2913, 2845, 1463, 1411, 1164, 1127, 1053, 945, 719 cm$^{-1}$; $^1$H-NMR (60 MHz, CDCl$_3$) δ (TMS) 5.1–4.8 (m, 1H, OCHO), 4.4–3.3 (m, 9H), 1.8–0.8 (m, approx. 47H).

Analysis calculated for C$_{29}$H$_{58}$O$_4$: C 73.98%; H 12.41%. Found: C 74.35%; H 12.71%.

c) (±)-cis, trans-8-[(2-heptadecyl-1,3-dioxolane-4-yl)methoxy]octyl 4-methylbenzenesulfonate Following the procedure described in example 1d, but using the compound obtained in example 20b instead of the compound obtained in example 1c, the desired product was obtained as a white solid in 79% yield after flash-chromatography purification (silica gel, ethyl acetate:hexane, 1:3).

mp : 45.9°–50.8° C.; IR (KBr) ν 2912, 2846, 1595, 1468, 1349,1184, 1170, 1109, 958, 838, 821, 718 cm$^{-1}$; $^1$N-NMR (60 MHz, CDCl$_3$)δ (TMS) 7.85 (d, J=8 Hz, 2H, Tos), 7.4 (d, J=8 Hz, 2H, Tos), 5.1–4.8 (m, 1H, OCHO), 4.4–3.7 (m), 3.7–3.3 (m), 2.5 (s, 3H, CH$_3$), 1.9–0.9 (m, approx. 47H).

Analysis calculated for C$_{36}$H$_{64}$O$_6$S: C 69.18%; H 10.32%. Found: C 69.01%; H 10.36%.

d) Preparation of the title compound of this example

Following the procedure described in example 1e, but using the compound obtained in example 20c instead of the compound obtained in example 1d, the title compound of this example was obtained as a white solid in 85% yield.

mp: 85°–97° C.; IR (KBr) ν 3650 (H$_2$O), 2915, 2847, 1636, 1484, 1214, 1200, 1122, 1034, 1011, 820, 683 cm$^{-1}$; $^1$H-NMR (60 MHz, CDCl$_3$)δ (TMS) 9.3–9.1 (m, 2H, pyr), 8.6–7.7 (m, 5H, pyr, Tos), 7.2 (d, J=8 Hz, 2H, Tos), 5.1–4.5 (m, 3H, OCHO, NCH$_2$), 4.4–3.3 (m, 7H, CH$_2$OCH$_2$CHCH$_2$), 2.35 (s, 3H, Tos-CH$_3$), 1.9–0.8 (m, approx. 47H).

Analysis calculated for C$_{41}$H$_{67}$NO$_6$S.H$_2$O: C 68.38%; H 9.65%; N 1.94%. Found: C 68.09%; H 9.58%; N 2.25%.

EXAMPLE 21

(±)-cis, trans-1-[8-[(2-pentadecyl-1,3-dioxolane-4-yl)methoxy)octyl]pyridinium 4-methylbenzenesulfonate Following the procedure described in example 20, but using hexadecanal instead of octadecanal, the title compound of this example was obtained in a similar yield.

EXAMPLE 22

(±)-cis, trans-3-[8-[(2-heptadecyl-1,3-dioxolane-4-yl)methoxy] octyl]thiazolium 4-methylbenzenesulfonate Following the procedure described in example 1e, but using the compound obtained in example 20c and thiazole instead of the compound obtained in example 1d and pyridine, the title compound of this example was obtained as a white solid in 78% yield.

mp: 56°–70° C.; IR (KBr) ν 3135, 2916, 2847, 1464, 1214, 1194, 1123, 1036, 1011, 817, 685 cm$^{-1}$, $^1$H-NMR (60 MHz, CDCl$_3$)δ (TMS) 10.6 (m, 1H, N=CHS), 8.4 (m, 2H, SCH=CHN), 7.8 (d, J=8 Hz, 2H, Tos), 7.2 (d, J=8 Hz, 2H, Tos), 5.1–4.8 (m, 1H, OCHO), 4.7–3.2 (m, 9H, NCH$_2$, CH$_2$OCH$_2$CHCH$_2$O), 2.4 (s, 3H, Tos-CH$_3$), 1.8–0.8 (m, approx. 47H)

Analysis calculated for $C_{39}H_{65}NO_6S_2 \cdot H_2O$: C 64.51%; H 9.30%; N 1.92%. Found: C 64.06%; H 9.31%; N 1.92%.

EXAMPLE 23

(±)-cis, trans-3-[8-[(2-pentadecyl-1,3-dioxolane-4-yl)methoxy]octyl]thiazolium 4-methylbenzenesulfonate Following the procedure described in example 22, but using hexadecanal instead of octadecanal, the title compound of this example was obtained in a similar yield.

EXAMPLE 24

(±)-cis, trans-1-[6-[(2-heptadecyl-1,3-dioxolane-4-yl)methoxy]-6-oxohexyl]pyridinium 4-methylbenzenesulfonate a) (±)-cis, trans-4-[((6-benzyloxy-1-oxohexyl)oxy)methyl]-2-heptadecyl-1,3-dioxolane To a cool solution (0° C.) of the compound obtained in example 1a (5.00 g, 14.5 mmol) and dry triethylamine (2.8 mL, 20 mmol) in dry dichloromethane (50 mL) was added ·6-(benzyloxy)hexanoyl chloride (4.33 g, 18.0 mmol). The reaction mixture was stirred at room temperature for 18 h and quenched by addition of 1M pH 7 phosphate buffer (50 mL). The organic layer was separated, dried over sodium sulfate, filtered and concentrated to give an oil. Flash-chromatography purification (silica gel, ethyl acetate : hexane, 1:7) afforded 6.74 g (85%) of pure product as a white wax. IR (KBr) v 2921, 2850, 1737, 1451, 1361, 1100, 734, 697 cm$^{-1}$; $^1$H-HMR (60 MHz, CDCl$_3$)δ (TMS) 7.35 (s, 5H, Ar), 5.1–4.8 (m, 1H, OCHO), 4.5 (s, 2H, AR–CH$_2$), 4.5–4.0 (m, 4H, O=COCCH$_2$CHCH), 4.0–3.7 (m, 1H, Me$_2$COCH(H)), 3.65–3.3 (m, 2H, BnOCH$_2$), 2.6–2.2 (m, 2H, O=CCH$_2$), 2.0–0.7 (m, approx. 41H).

Analysis calculated for $C_{34}H_{58}O_5$: C 74.67%; H 10.69%. Found: C 74.42%; H 11.04%.

b) (±)-cis, trans-[(2-heptadecyl-1,3-dioxolane-4-yl)methoxy]-6-oxo-1-hexanol

Following the procedure described in example 1c, but using the compound obtained in example 24a instead of the compound obtained in example 1b, the desired product was obtained as a white solid in 84% yield.

mp: 53.6°–55.7° C.; IR (KBr) v 3309, 2912, 2845, 1731, 1465, 1184, 718 cm$^{-1}$; $^1$H-NMR (60 MHz, CDCl$_3$)δ (TMS) 5.1–4.8 (m, 1H, OCHO), 4.5–4.0 (m), 4.0–3.5 (m), 2.5–2.2 (m, 3H, O=CCH$_2$, OH), 2.0–0.7 (m, approx. 41H).

Analysis calculated for $C_{27}H_{52}O_2$: C 71.00; %; H 11.47%. Found: C 70.88%; H 11.37%.

c) (±)-cis, trans-6-[(2-heptadecyl-1,3-dioxolane-4-yl)methoxy]-6-oxohexyl 4-methylbenzenesulfonate Following the procedure described in example 1d, but using the compound obtained in example 24b instead of the compound obtained in example 1c, the desired product was obtained as a white solid in 59% yield after flash-chromatography purification (silicia gel, ethyl acetate:hexane, 1:4).

mp: 41.9°–42.7° C.; IR (KBr) v 2914, 2847, 1734, 1596, 1478, 1467, 1392, 1237, 1175, 967, 835, 809, 669 cm$^{-1}$; $^1$H-NMR (60 MHz, CDCl$_3$)δ (TMS) 7.8 (d, J=8 Hz, 2H, Tos), 7.4 (d, J=8 Hz, 2H, Tos), 5.1–4.8 (m, 1H, OCHO), 4.6–3.7 (m, 7H), 2.4 (s, 3H, Tos-CH$_3$), 2.5–2.1 (m, 2H, O=CCH$_2$), 2.0–0.7 (m, approx. 41H).

Analysis calculated for $C_{34}H_{58}O_7S$: C 66.85%; H 9.57%. Found: C 66.445; H 9.87%.

d) Preparation of the title compound of this example

Following the procedure described in example 1e, but using the compound obtained in example 24c instead of the compound obtained in example 1d, the desired compound was obtained as a white solid in 87% yield.

mp 112°–115° C.; IR (KBr) v 3457 (H$_2$O), 3068, 2914, 2847, 1732, 1635, 1485, 1464, 1211, 1199, 1021, 1034, 825, 774, 683 cm$^{-1}$; $^1$H-NMR (60 MHz, CDCl$_3$)δ (TMS) 9.5–9.2 (m, 2H, pyr), 8.5–7.7 (m, 3H, Pyr), 7.8 (d, J=8 Hz, 2H, Tos), 7.2 (d, J=8 Hz, 2H, Tos), 5.1–4.5 (m, 3H, NCH$_2$, OCHO), 4.5–3.5 (m, 5H, O=COCH$_2$CHCH$_2$), 2.3 (s, 3H, Tos-CH$_3$), 2.5–2.0 (m, 2H, O=CCH$_2$), 2.0–0.7 (m, approx. 41H).

Analysis calculated for $C_{39}H_{63}NO_7S \cdot \frac{1}{2}H_2O$ : C 67.01%; H 9.22%; N 2.00%. Found: C 67.28%; H 9.67%; N 1.99%.

EXAMPLE 25

(±)-cis, trans-1-[6-[(2-pentadecyl-1,3-dioxolane-4-yl)methoxy]-6-oxohexyl]pyridinium 4-methylbenzenesulfonate Following the procedure described in example 24, but using hexadecanal instead of octadecanal, the title compound of this example was obtained in a similar yield.

EXAMPLE 26

(±)-cis, trans-3-[6-[(2-heptadecyl-1,3-dioxolane-4-yl)methoxy]-6-oxohexyl]-4-methylthiazolium 4-methylbenzenesulfonate Following the procedure described in example 1e, but using the compound obtained in example 24c and 4-methylthiazole instead of the compound obtained in example 1d and pyridine, respectively, the title compound of this example was obtained as a solid of cream color in 85% yield.

mp : 86°–89° C.; IR (KBr) v 3459 (H$_2$O), 3118, 2915, 2847, 1740, 1644, 1573, 1464, 1222, 1170, 1122, 1033, 1009, 821, 685 cm$^{-1}$; $^1$H-NMR (60 MHz, CDCl$_3$) δ(TMS) 10.7–10.5 (m, 1H, SCH=NO) 8.0–7.8 (m, 1H, SCH=C), 7.8 (d, J=8 Hz, 2H, Tos), 7.2 (d, J=8 Hz, 2H, Tos), 5.1–4.8 (m, 1H, OCHO), 4.7–3.5 (m, 7H, NCH$_2$, O=COCH$_2$CHCH$_2$), 2.5 (s, 3H, CH$_3$-thiazole), 2.3 (s, 3H, CH$_3$-Tos), 2.0–0.7 (m, approx. 41H).

Analysis calculated for $C_{38}H_{63}O_7S_2N \cdot 3/2H_2O$ : C 61.93%; H 9.03%; N 1.89%. Found : c 62.01%; H 8.83%; N 1.93%.

EXAMPLE 27

(±)-cis, trans-3-[6-[(2-heptadecyl-1,3-dioxolane-4-yl)methoxy]-6-oxohexyl]thiazolium 4-methylbenzenesulfonate Following the procedure described in example 1e, but using the compound obtained in example 24c and thiazole, instead of the compound obtained in example 1 and pyridine, respectively, the title compound of this example was obtained as a white solid in 68% yield. mp : 92.6°–95.3° C.; IR (KBr) v 3450 (H$_2$O), 3114, 2915, 2846, 1731, 1493, 1464, 1392, 1195, 1122, 1036, 1012, 820, 684 cm$^{-1}$; $^1$H-NMR (200 MHz, CDCl$_3$) δ(TMS) 10.7 (br s, 1H, N=CH-s), 8.31 (br d, 1H, thiazole), 8.2 (m, 1H, thiazole), 7.76 (d, J=8.2 Hz, 2H, Tos), 7.17 (d, J=8.2 Hz, 2H, Tos), 4.97 (t, J=4.9 Hz, 1H, OCHO, minor isomer), 4.89 (t, J=4.7 Hz, 1H, OCHO, major isomer), 4.68 (br t, J=7.0, 2H, NCH$_2$), 4.3–4.1 (m, 1H, O=COCH$_2$CHO), 4.09 (br t, J=6.2 Hz, 2H, O=COCH$_2$CHO), 3.91 (dd, J=6.9 Hz, J=8.4 Hz, 1H, O=COCH$_2$CHCH(H)O, major isomer), 3.74 (dd, J=4.9 Hz, J=8.4 Hz, 1H, O=COCH$_2$CHCH(H)O, major isomer), 3.57 (dd, J=6.6 Hz, J=8.4 Hz, 1H, O=COCH$_2$CHCH(H)O, minor isomer), 2.35 (s, 3H, Tos-CH$_3$), 2.29 (t, J=7 Hz, 2H, CH$_2$C=O), 1.92 (br quint., J=7 Hz, 2H), 1.7–1.5 (m, 4H), 1.5–1.2 (br s, approx. 32H), 0.88 (br t, 3H, CH$_3$).

Analysis calculated for C$_{37}$H$_{61}$NO$_7$S$_2$.½H$_2$O : C 63.44%; H 8.85%; N 2.00%. Found : C 63.52%; H 9.26%; N1.99%.

EXAMPLE 28

(±)-cis, trans-3-[6-[(2-pentadecyl-1,3-dioxolane-4-yl)methoxy]-6-oxohexyl]thiazolium 4-methylbenzenesulfonate Following the procedure described in example 27, but using hexadecanal instead of octadecanal, the title compound of this example was obtained in a similar yield.

EXAMPLE 29

(±)-cis, trans-3-[6-[(2-nonadecyl-1,3-dioxolane-4-yl)methoxyl]-6-oxohexyl]thiazolium 4-methylbenzenesulfonate Following the procedure described in example 27, but using eicosanal instead of octadecanal, the title compound of this example was obtained in a similar yield.

EXAMPLE 30

(±)-cis, trans-4-[6-[(2-heptadecyl-1,3-dioxolane-4-yl)methoxy]-6-oxohexyl]-4-methylmorpholinium 4-methylbenzenesulfonate Following the procedure described in example 1e, but using the compound obtained in example 24c and N-methylmorpholine, instead of the compound obtained in example 1d and pyridine, respectively, the title compound of this example was obtained as a cream-colored solid in 35% yield.

mp : 94°–106° C.; IR (KBr) ν 3451 (H$_2$O), 2915, 2848, 1735, 1464, 1201, 1121, 1035, 1010, 820, 683, 564 cm$^{-1}$; $^1$H-NMR (60 MHz, CDCl$_3$) δ(TMS) 7.8 (d, J=8 Hz, 2H, Tos), 7.15 (d, J=8 Hz, 2H, Tos), 5.1–4.8 (m, 1H, OCHO), 4.5–3.7 (m), 3.8–2.8 (m), 3.3 (s, 3H, NCH$_3$), 2.4–2.0 (m, 2H, O=CCH$_2$), 2.35 (s, 3H, CH$_3$-Tos), 1.9–0.7 (m, approx. 41H).

Analysis calculated for C$_{39}$H$_{69}$NO$_8$S.H$_2$O : C 64.17%; H 9.80; N 1.92%. Found : C 63.95%; H 10.06%; N 2.10%.

EXAMPLE 31

(±)-cis, trans-6-[(2-heptadecyl-1,3-dioxolane-4-yl)methoxy]-6-oxo-N,N,N-trimethyl-1-hexanaminium 4-methylbenzenesulfonate Following the procedure described in example 1e, but using the compound obtained in example 24c and a mixture of trimethylamine: acetonitrile (1:2), instead of the compound obtained in example 1d and pyridine, respectively, the title compound of this example was obtained as a white solid in 85% yield. mp : 141°–167° C.; IR (KBr) ν 3451 (H$_2$O), 3050, 2915, 2846, 1735, 1464, 1201, 1121, 1035, 1010, 820, 683, 564 cm$^{-1}$; $^1$-NMR (60 MHz, CDCl$_3$) δ(TMS) 7.8 (d, J=8 Hz, 2H, Tos), 7.2 (d, J=8 Hz, 2H, Tos), 5.1–4.8 (m, 1H, OCHO), 4.6–3.0 (m, 7H), 3.3 (s, 9H, (CH$_3$)$_3$N), 2.4–2.1 (m, 2H, O=CCH$_2$), 2.35 (s, 3H, CH$_3$-Tos), 2.0–0.7 (m, approx. 41H).

Analysis calculated for C$_{37}$H$_{67}$NO$_7$S.½H$_2$O : C 65.45%; H 10.09%; N 2.06%. Found : C 65.68%; H 10.31%; N 2.04%.

EXAMPLE 32

(±)-cis, trans-1-[6-[(2-heptadecyl-1,3-dioxolane-4-yl)methoxy]-6-oxohexyl]quinolinium 4-methylbenzenesulfonate Following the procedure described in example 1e, but using the compound obtained in example 24c and quinoline, instead of the compound obtained in example 1d and pyridine, respectively, the title compound of this example was obtained as a pink solid in 70% yield.

mp : 47°–52° C.; IR (KBr) ν 3447 (H$_2$O), 2914, 2846, 1731, 1622, 1594, 1525, 1464, 1196, 1033, 1011, 817, 775, 681 cm$^{-1}$; H-NMR (60 MHz, CDCl$_3$)δ(TMS) 10.1–9.9 (m, 1H, quin.), 9.3–9.0 (m, 1H, quin.), 8.5–7.8 (m, 5H, quin.), 7.84 (d, J=8 Hz, 2H, Tos), 7.13 (d, J=8 Hz, 2H, Tos), 5.4–4.7 (m, 3H, NCH$_2$, OCHO), 4.3–3.5 (m, 5H, O=COCH$_2$CHCH$_2$), 2.3 (s, 3H, Tos-CH$_3$), 2.5–2.0 (m, 2H, O=CCH$_2$), 2.0–0.7 (m, approx. 41H).

Analysis calculated for C$_{43}$H$_{65}$NO$_7$S.3H$_2$O : C 65.04%; H 9.01%; N 1.76%. Found : C 65.16%; H 8.65%; N 1.92%.

EXAMPLE 33

(±)-cis, trans-3-[4-[(2-heptadecyl-1,3-dioxolane-4-yl)methoxy]-4-oxobutyl]thiazolium 4-methylbenzenesulfonate Following the procedure described in example 27, but using 4-(p-toluenesulfonyloxy)butanoyl chloride, instead of 6-benzyloxy)hexanoyl chloride, and reacting the resulting product with thiazole, the title compound of this example was obtained in a similar yield.

EXAMPLE 34

(±)-cis, trans-3-[4-[(2-pentadecyl-1,3-dioxolane-4-yl)methoxy]-4-oxobutyl]thiazolium 4-methylbenzenesulfonate Following the procedure described in example 33, but using eicosanal instead of octadecanal, the title compound of this example was obtained in a similar yield.

EXAMPLE 35

(±)-cis, trans-3-[4-[(2-nonadecyl-1,3-dioxolane-4-yl)methoxy]-4-oxobutyl]thiazolium 4-methylbenzenesulfonate Following the procedure described in example 33, but using eicosanal instead of octadecanal, the title compound of this example was obtained in a similar yield.

EXAMPLE 36

(±)-cis,
trans-3-[5-[(2-heptadecyl-1,3-dioxolane-4-yl)methoxy]-
5-oxopentyl]thiazolium 4-methylbenzenesulfonate Following the procedure described in example 27, but using 5-(p-toluenesulfonyloxy) pentanoyl chloride instead of 5-(benzyloxy)hexanoyl chloride, and reacting the resulting product with thiazole, the title compound of this example was obtained in a similar yield.

EXAMPLE 37

(±)-cis,
trans-3-[7-[(2-heptadecyl-1,3-dioxolane-4-yl)methoxy]-
7-oxoheptyl]thiazolium 4-methylbenzenesulfonate Following the procedure described in example 27, but using 7-(benzyloxy)heptanoyl chloride instead of 6-(benzyloxy)hexanoyl chloride, the title compound of this example was obtained in a similar yield.

EXAMPLE 38

(±)-cis,
trans-3-[7-[(2-pentadecyl-1,3-dioxolane-4-yl)methoxy]-
7-oxoheptyl]thiazolium 4-methylbenzenesulfonate Following the procedure described in example 37, but using hexadecanal instead of octadecanal, the title compound of this example was obtained in a similar yield.

EXAMPLE 39

(±)-cis,
trans-3-[8-[(2-heptadecyl-1,3-dioxolane-4-yl)methoxy]-
8-oxooctyl]thiazolium 4-methylbenzenesulfonate Following the procedure described in example 27, but using 8-(benzyloxy)octanoyl chloride instead of 6-(benzyloxy)hexanoyl chloride, the title compound of this example was obtained in a similar yield.

EXAMPLE 40

(±)-cis,
trans-3-[6-[[(2-heptadecyl-1,3-dioxolane-4-yl)methoxycarbonyl]oxy]hexyl]thiazolium
4-methylbenzenesulfonate Following the procedure described in example 27, but using 6-(benzyloxy)hexyl chloroformate instead of 6-(benzyloxy)hexanoyl chloride, the title compound of this example was obtained in a similar yield.

EXAMPLE 41

(±)-cis,
trans-3-[6-[[(2-pentadecyl-1,3-dioxolane-4-yl)methoxycarbonyl]oxy]hexyl]thiazolium
4-methylbenzenesulfonate Following the procedure described in example 40, but using hexadecanal instead of octadecanal, the title compound of this example was obtained in a similar yield.

EXAMPLE 42

(±)-cis,
trans-3-[[4-[(2-pentadecyl-1,3-dioxolane-4-yl)methoxy]-
carbonyl]amino]butyl]thiazolium
4-methylbenzenesulfonate Following the procedure described in example 27, but using 4-(benzyloxy)butyl isocyanate instead of 6-(benzyloxy)hexanoyl chloride, the title compound of this example was obtained in a similar yield.

EXAMPLE 43

(±)-cis,
trans-3-[5-[[[(2-pentadecyl-1,3-dioxolane-4-yl)methoxy]carbonyl]amino]pentyl]thiazolium
4-methylbenzenesulfonate Following the procedure described in example 27, but using 5-(benzyloxy)pentyl isocyanate instead of 6-(benzyloxy)hexanoyl chloride, the title compound of this example was obtained in a similar yield.

EXAMPLE 44

(±)-cis,
trans-3-[5-[[[(2-pentadecyl-1,3-dioxolane-4-yl)methoxy]carbonyl]amino]pentyl]thiazolium
4-methylbenzenesulfonate Following the procedure described in example 43, but using hexadecanl instead of octadecanl, the title compound of this example was obtained in a similar yield.

EXAMPLE 45

(±)-cis,
trans-3-[6-[[[(2-heptadecyl-1,3-dioxolane-4-yl)methoxy]carbonyl]amino]hexyl]thiazolium
4-methylbenzenesulfonate Following the procedure described in example 27, but using 6-(benzyloxy)hexyl isocyanate instead of 6-(benzyloxy)hexanoyl chloride, the title compound of this example was obtained in a similar yield.

EXAMPLE 46

(±)-cis,
trans-3-[7-[[[(2-heptadecyl-1,3-dioxolane-4-yl)methoxy]carbonyl]amino]heptyl]thiazolium
4-methylbenzenesulfonate Following the procedure described in example 27, but using 7-(benzyloxy)heptyl isocyanate instead of 6-(benzyloxy)hexanoyl chloride, the title compound of this example was obtained in a similar yield.

EXAMPLE 47

(±)-cis,
trans-2-[[[(2-heptadecyl-1,3-dioxolane-4-yl)methoxy]-
hydroxyphosphinyl]oxy]-N,N,N-trimethylethanaminium hydroxide, inner salt a) Diester of 2-bromoethyl[2-heptadecyl-1,3-dioxolane-4-yl]methyl phosphoric acid To a solution of the compound obtained in example 1a (685 mg, 2 mmol) in dry carbon tetrachloride (7 mL), dry triethylamine (0.42 mL, 3 mmol) was added followed by 2-bromoethylphosphoryl dichloride (724 mg, 3 mmol) resulting in a white precipitate. The reaction mixture was stirred at room temperature for 1.5 h, filtered and concentrated. The residue was treated with a mixture of 0.5 M sodium acetate (23 mL) and tetrahydrofuran (23 mL) for 3 h. The major part of the tetrahydrofuran was evaporated in vacuo and the resulting aqueous residue was acidified to pH 1 with 1N HCl and was quickly extracted with ether. The organic phase was dried over anhydrous sodium sulfate and was concentrated to give an oil that crystallized with ethyl acetate. The product obtained in that way was used in next step without further purification. A pure analytical sample can be obtained by flash-chromatography purification (silica gel, chloroform: methanol, 5:1) as a white solid.

mp : 54.8°–55.4° C.; IR (KBr) v 3445, 2916, 2847, 1464, 1232, 1119, 955 cm$^{-1}$.

b) Preparation of the title compound of this example

To a solution of the compound obtained in example 47a in dry chloroform (13 mL) was added a mixture of trimethylamine: acetonitrile (1:2) (22 mL) and the solution was refluxed for 3 h. After evaporation of the solvents, the resulting residue was dissolved in methanol (11 mL) and was treated with silver carbonate (150 mg) and IRP-58 Amberlite resin (600 mg) at room temperature for 2 h. After filtering and purification by flash-chromatography (silica gel, chloroform: methanol: water, 14:6:1) 320 mg (31% yield) of the title compound of this example was obtained as a white solid.

mp : 145° C.; IR (KBr) v 3417 (H$_2$O), 2914, 2846, 1649, 1465, 1246, 1127, 1089, 1055 cm$^{-1}$; $^1$H-NMR (200 MHz, CD$_3$OD δ(TMS) 4.98 (t, J=7 Hz, OCHO, minor isomer), 4.85 (t, J=7 Hz, OCHO, major isomer), 4.35–4.20 (m, 3H, OCHCH$_2$OP), 3.95–3.80 (m, 4H, OCH$_2$CHCH$_2$), 3.67–3.59 (m, 2H, NCH$_2$), 3.22 (s, 9H, (CH$_3$)$_3$N), 1.7–1.5 (m, 2H, RCH$_2$CHO), 1.25 (s, approx. 29H, (CH$_2$)$_n$), 0.88 (t, J=7 Hz, 3H, CH$_3$).

Analysis calculated for C$_{26}$H$_{54}$NO$_6$P.2H$_2$O : C 57.43%; H 10.75%; N 2.57%. Found : C 57.83%; H 11.10; N 2.27%.

EXAMPLE 48

(±)-cis, trans-1-[2-[[[(2-heptadecyl-1,3-dioxolane-4yl)methoxy]-hydroxyphosphinyl]oxy]ethyl]pyridinium hydroxide, inner salt Following the procedure described in example 47b, but using pyridine (2 mL) instead of a mixture chloroform:trimethylamine: acetonitrile, the title compound of this example was obtained as a hygroscopic solid of cream color in 27% yield.

mp : 85°–92° C.; IR (KBr) v 3403 (H$_2$O), 3133, 3046, 2917, 2847, 1684, 1633, 1487, 1464, 1260, 1237, 1046, 924 cm$^{-1}$; $^1$H-NMR (60 MHz, CDCl$_3$) δ(TMS) 9.3–9.0 (m, 2H, pyr), 8.6–8.3 (m, 1H, pyr), 8.2–7.9 (m, 2H, pry), 5.2–4.7 (m, 3H, NCH$_2$, OCHO), 4.7–3.5 (m), 3.5–3.0 (m), 1.8–0.8 (m, approx. 35H).

Analysis calculated for C$_{28}$H$_{50}$NO$_6$P.3/2H$_2$O : C 60.65%; H 9.63%; N 2.52%. Found : C 60.70%; H 9.77%; N 2.78%.

EXAMPLE 49

(±)-cis, trans-3-[2-[[[(2-heptadecyl-1,3-dioxolane-4-yl)methoxy]hydroxyphosphinyl]oxy]ethyl]thiazolium hydroxide, inner salt Following the procedure described in example 47, but using thiazole instead of a mixture of triethylamine: chloroform: acetonitrile, the title compound of this example was obtained in a similar yield.

EXAMPLE 50

(±)-cis, trans-3-[2-[[[(2-pentadecyl-1,3-dioxolane-4-yl)methoxy]hydroxyphosphinyl]oxy]ethyl]thiazolium hydroxide, inner salt Following the procedure described in example 49, but using hexadecanal instead of octadecanal, the title compound of this example was obtained in a similar yield.

EXAMPLE 51

(±)-cis, trans-3-[3-[[[(2-heptadecyl-1,3-dioxolane-4-yl)methoxy]hydroxyphosphinyl]oxy]propyl]thiazolium hydroxide, inner salt Following the procedure described in example 49, but using the 3-bromopropylic phosphoric ester instead of the 2-bromoethylic phosphoric ester as the starting material, the title compound of this example was obtained in a similar yield.

We claim:

1. 2,4-Disubstituted 1,3-dioxolanes of formula

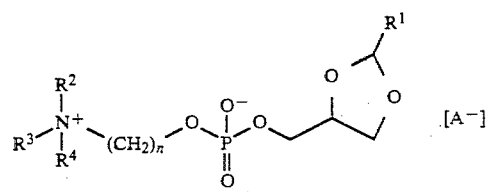

wherein:

R$^1$ represents a linear or branched alkyl, alkenyl or alkynyl group, of 10 to 24 carbon atoms;

n is an integer 2 to 10; and

R$^2$, R$^3$, and R$^4$ are lower alkyl groups (with the proviso that when R$^1$ is n—C$_{15}$H$_{29}$, n—C$_{17}$H$_{33}$, then R$^2$, R$^3$, and R$^4$ are not simultaneously all methyl) or R$^2$R$^3$R$^4$N+ represents an aromatic cyclic ammonium group selected from the group consisting of thiazolium, benzothiazolium, oxazolium, pyridinium, quinolinium or isoquinolinium.

2. 2,4-Disubstituted 1,3-dioxolanes of formula

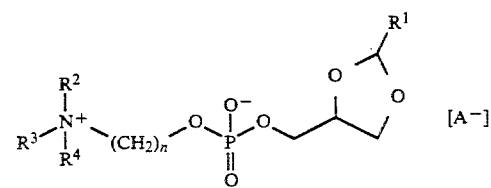

wherein:

R$^1$ represents a linear or branched alkyl, alkenyl or alkynyl group, of 10 to 24 carbon atoms;

n is an integer 2 to 10 ; and

R$^2$, R$^3$, and R$^4$ are lower alkyl groups (with the proviso that when R$^1$ is n—C$_{15}$H$_{31}$, n—C$_{17}$H$_{33}$, then R$^2$, R$^3$, and R$^4$ are not simultaneously all methyl) or R$^2$R$^3$R$^4$R+ represents an aromatic cyclic ammonium group selected from the group consisting of thiazolium, benzothiazolium, oxazolium, pyridinium, quinolinium or isoquinolinium optionally ring-substituted with lower alkyl, hydroxyl, lower hydroxyalkyl, amino, lower aminoalkyl, carbamoyl or ureido.

3. 2,4-Disubstituted 1,3-dioxolanes of formula I

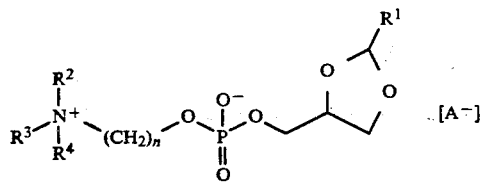

wherein:

R¹ represents a linear or branched alkyl, alkenyl or alkynyl group, of 10 to 24 carbon atoms;

n is an integer 2 to 10; and

R², R³, and R⁴ are lower alkyl groups (with the proviso that when R¹ is n—$C_{15}H_{31}$, n—$C_{17}H_{33}$, then R², R³, and R⁴ are not simultaneously all methyl) or $R^2R^3R^4N^+$ represents an aromatic cyclic ammonium group selected from the group consisting of thiazolium, benzothiazolium, oxazolium, pyridinium, quinolinium or isoquinolinium optionally ring-substituted with lower alkyl, hydroxyl, lower hydroxyalkyl, amino, lower aminoalkyl, carbamoyl or ureido, or $R^2R^3R^4N^+$ represents a non-aromatic cyclic group in which two of the substituents (R², R³, or R⁴, which are lower alkyl groups) form a ring together with the nitrogen atom, and the remaining group is hydrogen or lower alkyl.

* * * * *

UNITED STATES PATENT AND TRADEMARK OFFICE
CERTIFICATE OF CORRECTION

PATENT NO. : 5,070,139

DATED : December 3, 1991

INVENTOR(S) : Javier Bartroli et al.

It is certified that error appears in the above-identified patent and that said Letters Patent is hereby corrected as shown below:

In the abstract, line 10 "$R^2R^3R^4N^{30}$" should be --$R^2R^3R^4N^+$--.

Col. 1, line 39 "ucts" should be --uce--.

Col. 15, line 1 "tetrahydrofuan" should be --tetrahydrofuran--.

Col. 16, line 4 "in" should be --it--.

Col. 17, line 55 "pyridien" should be --pyridine--.

Col. 18, line 15 "-C(=O)-O-C(" should be -- -C(=O), -O-C(--.

Col. 18, line 45 "sayd" should be --say--.

Col. 19, line 44 "carotide" should be --carotid--.

Col. 20, line 6 "After" should be --after--.

Col. 20, line 34 "hydroxypyropylcellulose" should be --hydroxypropylcellulose--.

Col. 21, line 24 "for" (first occurence) should be --form--.

Col. 23, line 11 "KBv" should be --KBr--.

Col. 23, line 32 "KBv" should be --KBr--.

Col. 23, line 63 "he" should be --the--.

Col. 23, line 67 "KBv" should be --KBr--.

Col. 28, line 30 "815 16" should be --816--.

UNITED STATES PATENT AND TRADEMARK OFFICE
CERTIFICATE OF CORRECTION

PATENT NO. : 5,070,139

DATED : December 3, 1991

INVENTOR(S) : Javier Bartroli et al.

It is certified that error appears in the above-identified patent and that said Letters Patent is hereby corrected as shown below:

Col. 28, line 31 "$cm^{31}$" should be --$cm^{-1}$--.

Col. 29, line 45 "2heptadecyl-1,3-dioxolane" should be --2-heptadecyl-1,3-dioxolane.--.

Col. 30, line 68 "47H)" should be --47H).--.

Col. 32, line 49 "SCH=NO" should be --SCH=N--.

Col. 32, line 56 "c" should be --C--.

Col. 36, line 21 "hexadecanl" should be --hexadecanal-- and "octadecanl" should be --octadecanal--.

Col. 38, line 62 "$n-C_{15}H^{31}$" should be --$n-C_{15}H_{31}$--.

Col. 38, line 64 "$R^2R^3R^4R+$" should be --$R^2R^3R^4N^+$--.

Col. 40, line 3 (claim 3) "$n-C_{15}H^{31}$" should be --$n-C_{15}H_{3.}$--.

Signed and Sealed this

Twelfth Day of October, 1993

Attest:

BRUCE LEHMAN

*Attesting Officer*     *Commissioner of Patents and Trademarks*